(12) United States Patent
Rowe et al.

(10) Patent No.: US 6,699,504 B2
(45) Date of Patent: Mar. 2, 2004

(54) SLOW RELEASE PROTEIN POLYMERS

(75) Inventors: Stephen C. Rowe, Wellesley, MA (US); Kalvin Yim, North Andover, MA (US); Beadle P. Retnarajan, Beverly, MA (US); Jeffrey A. Hubbell, Zumikon (CH); Durga Annavajula, Acton, MA (US)

(73) Assignee: Pelias Technologies, Inc., Washington, DC (US)

( * ) Notice: Subject to any disclaimer, the term of this patent is extended or adjusted under 35 U.S.C. 154(b) by 52 days.

(21) Appl. No.: 09/772,174

(22) Filed: Jan. 29, 2001

(65) Prior Publication Data

US 2001/0048947 A1 Dec. 6, 2001

Related U.S. Application Data

(60) Provisional application No. 60/178,852, filed on Jan. 28, 2000.

(51) Int. Cl.$^7$ .............. A61K 9/14; A61K 9/50; A61F 2/02
(52) U.S. Cl. .......... 424/486; 424/424; 424/425; 424/426; 424/501; 424/50
(58) Field of Search ................ 424/423, 424, 424/425, 426, 486, 501, 502

(56) References Cited

U.S. PATENT DOCUMENTS

| | | | |
|---|---|---|---|
| 5,410,016 A | * 4/1995 | Hubbell et al. | 528/354 |
| 5,879,713 A | 3/1999 | Roth et al. | 424/489 |
| 6,007,833 A | 12/1999 | Chudzik et al. | 424/425 |
| 6,156,345 A | 12/2000 | Chudzik et al. | 424/484 |

* cited by examiner

*Primary Examiner*—Carlos A. Azpuru
(74) *Attorney, Agent, or Firm*—Clark & Elbing, LLP; Kristina Bieker-Brady

(57) ABSTRACT

The invention features articles for delivery of a biologically active substance, methods for making such articles, and methods for treating an animal using the articles.

77 Claims, 7 Drawing Sheets

SLOW RELEASE PROTEIN POLYMERS

CROSS REFERENCE TO RELATED APPLICATIONS

This application claims priority from U.S. Ser. No. 60/178,852, filed Jan. 28, 2000, entitled "Slow Release Protein Polymers," having as inventors Steven C. Rowe, Kalvin Yim, Beadle P. Retnarajan, and Jeffrey A. Hubbell.

BACKGROUND OF THE INVENTION

The invention relates to biodegradable compositions for sustained-release drug delivery and methods for administering a biologically active substance via these compositions.

Rapid advances in the fields of genetic engineering and biotechnology have led to the development of an increasing number of proteins and polypeptides that are useful as pharmaceutical agents. The development of methods for administering these new pharmaceutical agents is thus becoming increasingly important.

Most proteins have relatively short half-lives, requiring frequent administration to achieve efficacious blood levels. To increase patient convenience and to improve efficacy and safety by keeping blood levels within the therapeutic range, smoothly releasing injectable depot formulations of protein drugs are highly desirable.

Recent polymer developments have improved the ability to deliver proteins and peptides by allowing for slower and steadier release of the molecule in the patient's system. However, in many cases, the active form of the protein is difficult to formulate in biodegradable polymers. Synthetic materials, such as biodegradable hydrogels, have also been developed for use in delivering proteins. Despite the advances provided by the available polymers and hydrogels, the delivery of protein to the systemic and local circulation is still relatively rapid, in some cases too rapid to allow this route of administration to be used.

SUMMARY OF THE INVENTION

The present invention features articles for delivery of a biologically active substance (hereafter "BAS"), and methods for making such articles. The articles of the invention improve the bioavailability of the BAS by formulating the BAS in an insoluble form. The invention also features methods of treating an animal using the articles for delivery of a BAS.

Accordingly, in a first aspect the invention features a biocompatible therapeutic article for delivery of a BAS, comprising a macromer, a molecule or mixture of molecules which preferentially excludes proteins, and the BAS, wherein the BAS is in an insoluble format upon completion of the formulation of the article comprising the macromer, molecule, or mixture of molecules which preferentially excludes proteins, and BAS.

In a preferred embodiment of the first aspect of the invention, the biocompatible therapeutic article has at least one of the following properties: the BAS is less than 15% aggregated; the article contains at least 10% macromer and at least 5% BAS, as measured by dry weight; the time at which 5% of the releasable BAS is released from the article is greater than $1/16$ of $t_{50}$; or the $t_{50}$ is greater than or equal to $5/8$ of $t_{80}$. More preferably the biocompatible therapeutic article has at least two of the above properties. Most preferably, the biocompatible therapeutic article has all of the above properties.

In another embodiment of the first aspect of the invention, the molecule which preferentially excludes proteins is a macromer, poly(ethylene glycol), hyaluronic acid, or poly(vinylpyrrolidone). In yet another embodiment, the macromer is a hydrogel. In still another embodiment, the solubility of a protein in the article comprising the macromer, molecule that preferentially excludes proteins, and BAS is less than 5–10 mg/ml, and more preferably is less than 1 mg/ml.

In another embodiment of the first aspect of the invention, the mixture of molecules comprises a positively charged ion-carrying reagent, for example, triethanolamine or Tris, when the pH is such that the protein is negatively charged. In still another embodiment, the mixture of molecules comprises a negatively charged ion-carrying reagent, such as sodium dodecyl sulfate, when the pH is such that the protein is positively charged. In yet another embodiment, the mixture of molecules comprises a surfactant, for example, Tween 20, Tween 80, or poloxamer F68. In a second aspect, the invention features a method for making a therapeutic article for delivery of a BAS, involving (a) combining the BAS with a molecule or mixture of molecules which preferentially excludes proteins; (b) combining the mixture formed in step (a) with a macromer, wherein the BAS is in an insoluble form and remains insoluble upon combining with the molecule or mixture of molecules which preferentially excludes proteins and the macromer; (c) forming a mixture of the combination formed in step (b); and (d) polymerizing the mixture to form an article.

In one embodiment of the second aspect of the invention, steps (a) and (b) are combined into a single combination step.

In a preferred embodiment of the second aspect of the invention, the biocompatible therapeutic article has at least one of the following properties: the BAS is less than 15% aggregated; the article contains at least 10% macromer and at least 5% BAS, as measured by dry weight; the time at which 5% of the releasable BAS is released from the article is greater than $1/16$ of $t_{50}$; or the $t_{50}$ is greater than or equal to $5/8$ of $t_{80}$. More preferably the biocompatible therapeutic article has at least two of the above properties. Most preferably, the biocompatible therapeutic article has all of the above properties.

In another embodiment of the second aspect of the invention, the molecule which preferentially excludes proteins is a macromer, poly(ethylene glycol), hyaluronic acid, or poly(vinylpyrrolidone). In yet another embodiment, the macromer is a hydrogel. In yet another embodiment, the macromer is a hydrogel. In still another embodiment, the solubility of a protein in the article comprising the macromer, molecule that preferentially excludes proteins, and BAS is less than 5–10 mg/ml, and more preferably is less than 1 mg/ml.

In another embodiment of the second aspect of the invention, the mixture of molecules comprises a positively charged ion-carrying reagent, for example, triethanolamine, when the pH is such that the protein is negatively charged. In still another embodiment, the mixture of molecules comprises a negatively charged ion-carrying reagent, such as sodium dodecyl sulfate, when the pH is such that the protein is positively charged. In yet another embodiment, the mixture comprises a surfactant, for example, Tween 20, Tween 80, or poloxamer F68.

In a third aspect the invention features a method of treating an animal, involving administering the biocompatible therapeutic article of the first aspect of the invention to a mammal. Preferably the mammal is a rodent, and most preferably the mammal is a human.

In yet other preferred embodiments, the articles are administered to the lung of the mammal, or are administered intravenously, subcutaneously, intramuscularly, orally, or nasally.

In a preferred embodiment of any of the above aspects of the invention, the macromer comprises: (a) a region forming a central core; (b) at least two degradable regions attached to the core; and (c) at least two polymerizable end groups, where the polymerizable end groups are attached to the degradable regions. In preferred embodiments, the region forming a central core is a water soluble region. The water soluble region may be poly(ethylene glycol), poly(ethylene oxide), poly(vinyl alcohol), poly(vinylpyrrolidone), poly (ethyloxazoline), poly(ethylene oxide)-co-poly(propylene oxide) block copolymers, polysaccharides, carbohydrates, proteins, and combinations thereof. The degradable region is selected from the group consisting of poly($\alpha$-hydroxy acids), poly(lactones), poly(amino acids), poly(anhydrides), poly(orthoesters), poly(orthocarbonates), and poly (phosphoesters). Preferably, the poly($\alpha$-hydroxy acid) is poly(glycolic acid), poly(DL-lactic acid), or poly(L-lactic acid), and the poly(lactone) is poly($\epsilon$-caprolactone), poly($\delta$-valerolactone), or poly($\gamma$-butyrolactone). In another preferred embodiment, the degradable region comprises poly (caprolactone). In yet another embodiment, the polymerizable end groups contain a carbon—carbon double bond capable of polymerizing the macromer.

In other embodiments of the above aspects of the invention, the macromer includes: (a) a water soluble region comprising a three-armed poly(ethylene glycol) with a molecular weight of 3,000 to 6,000 daltons; (b) lactate groups attached to the region in (a); and (c) acrylate groups capping the region in (b). The macromer may alternatively include: (a) a water soluble region comprising poly(ethylene glycol) with a molecular weight of either 2,000 or 3,400 daltons; (b) lactate groups on either side of the region in (a); and (c) acrylate groups capping either side of the region in (b). In another alternative, the macromer may include (a) a water soluble region comprising poly(ethylene glycol) with a molecular weight of 3,400 daltons; (b) caprolactone groups on either side of region in (a); and (c) acrylate groups capping either side of the region in (b).

In still other embodiments of any of the above aspects of the invention, the article includes at least 5%, more preferably 10%, and most preferably 20–30% active substance by dry weight. In still another embodiment, the article is biodegradable.

In a more preferred embodiment of any of the above aspects of the invention, the macromer includes a water soluble region consisting of a three-armed PEG with a molecular weight of 4,200 to 5,400 daltons; lactate groups one end of each arm of the PEG; and acrylate groups capping the lactate groups.

In another more preferred embodiment of the above aspects of the invention, the macromer is made of a triad ABA block copolymer of acrylate-poly(lactic acid)-PEG-acrylate-poly(lactic acid)-acrylate. The PEG has a MW of 3,400 daltons; the poly(lactic acids) on both sides had an average of about five lactate units per side; and the macromer is therefore referred to herein as "3.4kL5." In another more preferred embodiment, a lower molecular weight PEG, such as MW 2,000 daltons PEG is used in place of the MW 3,400 PEG, and the resulting macromer is abbreviated as "2kL5."

In yet another more preferred embodiment of the above aspects of then invention, the macromer is an acrylate-PCL-PEG-PCL-acrylate macromer. The PEG has a MW of 3,400 daltons and has polycaprolactone on both sides, with an average of about 6 caproyl units per side. This macromer is referred to herein as "3.4kC6."

In other preferred embodiments, the BAS is a protein or peptide. More preferably the protein is chosen from a group consisting of hormones, antibodies, differentiation factors, angiogenic factors, enzymes, cytokines, chemokines, interferons, colony-stimulating factors, and growth factors. Most preferably, the protein is a hormone, such as human growth hormone, or a peptide, such as LHRH.

In still other embodiments of the second and third aspects of the invention, the therapeutic articles release at least 80% of the BAS at a time 1¼ times greater than $t_{50}$. At least 80% of the therapeutic articles may have a particle size of less than about 80 microns. The water soluble region may consist essentially of PEG having a molecular weight of about 500 to 20,000 daltons, and more preferably, between 1,000 and 10,000 daltons. The degradable region may comprise a blend of at least two different polymers. In addition, the macromer may be non-degradable.

In still other embodiments of the second and third aspects of the invention, the therapeutic article is capable of releasing the BAS for at for a period of time at least 2 times greater than $t_{50}$. The article is also capable of delivering a therapeutic dose of the BAS for at for a period of time at least 1¼ times greater than $t_{50}$.

By "macromer" is meant a polymer with three components: (1) a biocompatible, water soluble region; (2) a biodegradable/hydrolyzable region, and (3) at least two polymerizable regions.

By "biologically active substance" or "BAS" is meant a compound, be it naturally-occurring or artificially-derived, that is incorporated into an article and which may be released and delivered to a site. Biologically active substances may include, for example, peptides, polypeptide, proteins, synthetic organic molecules, naturally occurring organic molecules, nucleic acid molecules, and components thereof.

By "a molecule or mixture of molecules that preferentially excludes proteins" is meant a molecule or mixture of molecules, be it naturally-occurring or artificially-derived, that, when added to a solution, confers a lower level of solubility of the protein or polypeptide in said solution. Preferably, protein solubility will be decreased 50-fold; more preferably, 100-fold and most preferably about 200-fold. Preferably the solubility of a protein in a solution that includes said molecule or mixture of molecules that preferentially excludes proteins is less than 5–10 mg/ml, and more preferably is less than 1 mg/ml.

By "substantially pure polypeptide" or "protein" is meant a polypeptide or protein that has been separated from the components that naturally accompany it. The terms polypeptide and protein may be used interchangeably. Typically, the polypeptide is substantially pure when it is at least 60%, by weight, free from the proteins and naturally-occurring organic molecules with which it is naturally associated. A substantially pure polypeptide may be obtained, for example, by extraction from a natural source (e.g., a cell expressing the desired polypeptide), by expression of a recombinant nucleic acid encoding a desired polypeptide, or by chemically synthesizing the polypeptide. Purity can be assayed by any appropriate method, e.g., by column chromatography, polyacrylamide gel electrophoresis, agarose gel electrophoresis, optical density, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "purified nucleic acid" is meant a nucleic acid that is free of the genes which, in the naturally-occurring genome of the organism from which the nucleic acid of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes recombinant DNA which is part of a hybrid gene encoding additional polypeptide sequence.

By "biocompatible" is meant that any compound or substance which is administered to a subject, cell, or tissue is used to treat, replace, or augment a function of the subject, cell or tissue, and is not harmful to said function.

By "insoluble" is meant that the solubility of a compound is less than 1 g/100 ml in a solution. The solution may be an aqueous solution, an organic solvent, such as dimethylsulfoxide, or a mixture of aqueous and organic solvents. As used herein, a BAS is in an insoluble format upon completion of the formulation for a therapeutic article for delivery of the BAS. The BAS remains in an insoluble format upon delivery of the therapeutic article to a patient, and is then slowly released at a controlled rate for localized or systemic delivery to the patient.

As used herein, by "aggregated" is meant that a BAS is releasable as individual molecules. The percent of a BAS in an article which is aggregated can be determined, for example, by SEC-HPLC.

By "therapeutic dose," when referring to a BAS, is meant a plasma level between the minimum effective level and the toxic level.

By a "mixture" is meant a composition in which all of the compounds contained in the composition are evenly distributed.

As used herein, by "pore size" is meant the dimensions of a space in the intact polymer through which a macromer, component of a macromer, or a BAS potentially can pass. Pore sizes which are utilized as part of the invention are those smaller than the BAS as it is present in the particular embodiment (e.g., a protein molecule, or aggregate thereof).

As used herein, by "period of release" is meant the length of time it takes for a specified percent of the BAS to be released from an article. The period of release may be assessed, for example, by measuring the time it takes for 50% or 80% of the BAS to be released from the article.

By "low burst effect" is meant that the amount of BAS released from an article is released relatively steadily over time, rather than at an initial fast rate, followed by a slower rate. For example, a BAS has a low burst effect (e.g., less than or equal to 20% burst) upon release from an article when the period of release for 5% of the releasable BAS is greater than $1/16$ of $t_{50}$, or when the $t_{50}$ is greater than or equal to $5/8$ of $t_{80}$. In contrast to a low burst article, a high burst article (e.g., one which rapidly releases 30% of the BAS) might release 5% of its releasable BAS in less than $1/18$ of $t_{50}$ and have a $t_{50}$ equal to $1/2$ of $t_{80}$.

A specific example of a low burst product of the present invention is one in which less than 20% of the BAS comes out in the first day for a product designed to release a BAS for 10 days.

By "$t_{50}$" is meant the time at which 50% of the original load of BAS has been released. As used herein, preferably 5% of the releasable BAS is released at a time which is greater than $1/16$ of $t_{50}$, or the $t_{50}$ is greater than or equal to $5/8$ of the $t_{80}$.

By "$t_{80}$" is meant the time at which 80% of the original load of BAS has been released. As used herein, preferably 5% of the releasable BAS is released at a time which is greater than $1/16$ of $t_{50}$, or the $t_{50}$ is greater than or equal to $5/8$ of the $t_{80}$.

DETAILED DESCRIPTION

Figure 1:
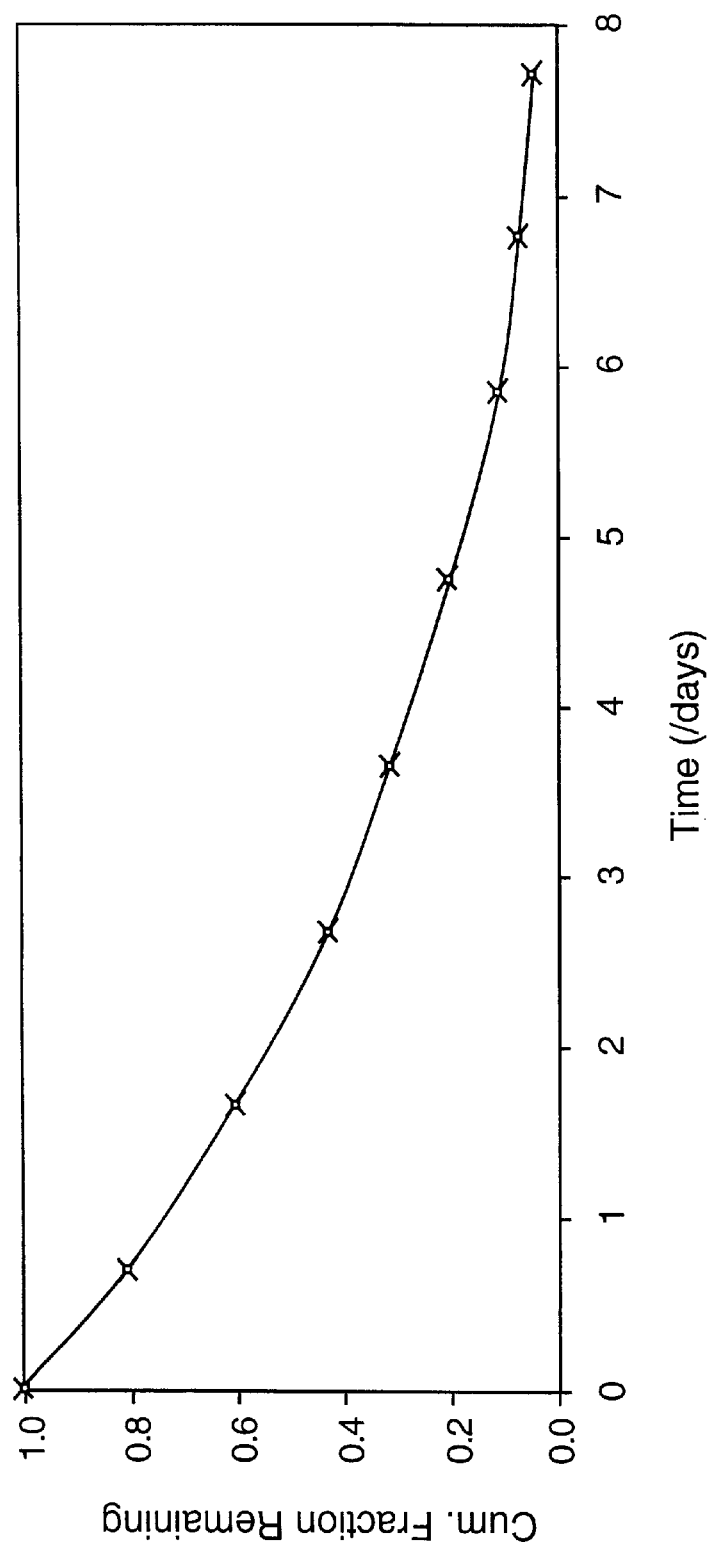
FIG. 1 is the release profile of microspheres made with precipitated hGH.

The invention provides methods and compositions for the administration of a biologically active substance (BAS) in an insoluble format. The compositions of the invention improve the bioavailability of the BAS by formulating the BAS in an insoluble format. These methods and compositions provide for the controlled, sustained delivery of relatively large quantities of these substances, with a low burst effect.

Macromers

The macromers of the present invention have at least one region forming a central core, at least one degradable (e.g., hydrolyzable) region, and at least one polymerizable region. The macromers may be water-soluble or water insoluble. Preferably, the region forming a central core is water soluble. If desired, the macromers may be polymerized to form hydrogels, which are useful for delivering incorporated substances at a controlled rate. Methods to formulate macromers and shape them into articles are described, for example in WO 99/03454, hereby incorporated by reference. An important aspect of the macromers is that the polymerizable regions are separated by at least one degradable region. This separation facilitates uniform degradation in vivo.

The ratio between the central core region and the hydrolyzable region of the macromer determines many of the general properties of the macromer. For example, the water solubility of the macromers can be controlled by varying the percentage of the macromer that consists of hydrophobic degradable groups.

There are several variations of the macromers of the present invention. For example, the polymerizable regions can be attached directly to the degradable regions; alternatively, they can be attached indirectly via water-soluble, nondegradable regions, with the polymerizable regions separated by a degradable region. For example, if the macromer contains a single water-soluble region coupled to a degradable region, one polymerizable region can be attached to the water-soluble region, and the other to the degradable region.

In another embodiment, a water-soluble region forms the central core of the macromer and has at least two degradable regions attached to it. At least two polymerizable regions are attached to the degradable regions so that, upon degradation, the polymerizable regions, particularly in the polymerized gel form, are separated. Alternatively, if the central core of the macromer is formed by a degradable region, at least two water soluble regions can be attached to the core, and polymerizable regions are attached to each water soluble region.

In still another embodiment, the macromer has a water-soluble backbone region, with a degradable region attached to the macromer backbone. At least two polymerizable regions are attached to the degradable regions, such that they are separated upon degradation, resulting in gel product dissolution. In a further embodiment, the macromer backbone region is formed of a degradable backbone region having water-soluble regions as branches or grafts attached to the degradable backbone. Two or more polymerizable regions are attached to the water soluble branches or grafts.

In another variation, the macromer backbone may have multiple arms; e.g., it may be star-shaped or comb-shaped. The backbone may include a water-soluble region, a biodegradable region, or a water-soluble, biodegradable region. The polymerizable regions are attached to this backbone. Again, the polymerizable regions must be separated at some point by a degradable region.

Throughout the specification, the following abbreviations are sometimes used to describe the specific macromers of the invention. In three particular examples, a macromer having a water soluble region consisting of PEG with a molecular weight of 4,000 daltons, with 5 lactate groups on either side of this region, capped on either side with acrylate groups, is referred to as "4kL5." Similarly, a macromer having a water soluble region consisting of PEG with a molecular weight of 3,400 daltons, with 6 caprolactone groups on either side of this region, capped on either side with acrylate groups, is referred to as "3.4kC6." Likewise, a macromer having a water soluble region consisting of PEG having a molecular weight of 5,400 daltons and 3 arms, each arm containing 3 lactate groups, extending from this region, capped on either side with acrylate groups, is referred to as "4.2kL3-A3."

Water-Soluble Region

In preferred embodiments, the central core is a water soluble region. This water soluble region of the macromer may include poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, polysaccharides, carbohydrates, or proteins, or combinations thereof.

The macromer preferably comprises a water soluble core region comprising PEG, as PEG has high hydrophilicity and water solubility, as well as good biocompatibility. The PEG region preferably has a molecular weight of about 400 to about 40,000 daltons, and more preferably has a molecular weight of about 1,000 to about 30,000 daltons, about 1,000 to about 20,000 daltons, or about 2,000 to about 10,000 daltons.

Degradable Region

The degradable region of the macromer may contain, for example, poly($\alpha$-hydroxy acids), poly(lactones), poly(amino acids), poly(anhydrides), poly(orthoesters), poly(orthocarbonates) or poly(phosphoesters), or blends or copolymers of these polymers.

Exemplary poly($\alpha$-hydroxy acids) include poly(glycolic acid), poly(DL-lactic acid), and poly(L-lactic acid). Exemplary poly(lactones) include poly($\epsilon$-caprolactone), poly($\delta$-valerolactone), poly($\gamma$-butyrolactone), poly(1,5-dioxepan-2-one), and poly(trimethylene carbonate).

The degradable region may comprise a blend of at least two different polymers. Examples of copolymers include a copolymer of caprolactone and glycolic acid; and a copolymer of caprolactone and lactic acid.

Polymerizable Region

The polymerizable regions of the macromer preferably contain carbon—carbon double bonds capable of polymerizing the macromers. The choice of an appropriate polymerizable group permits rapid polymerization and gelation. Polymerizable regions containing acrylates are preferred because they can be polymerized using several initiating systems, as discussed below. Examples of acrylates include acrylate, methacrylate, and methyl methacrylate.

Polymerization of Macromers

If desired, the macromers of the present invention may be polymerized using polymerization initiators under the influence of long wavelength ultraviolet light, visible light, thermal energy, or a redox system. The polymerization can be conducted at room temperature or at lower temperatures, for example, temperatures less than 20° C. During polymerization, substances such as proteins are physically incorporated into the resulting polymer network of the hydrogel.

Polymerization of the macromers may be initiated in situ by light having a wavelength of 320 nm or longer. When the polymerizable region contains acrylate groups, the initiator may be any of a number of suitable dyes, such as xanthine dyes, acridine dyes, thiazine dyes, phenazine dyes, camphorquinone dyes, acetophenone dyes, or eosin dyes with triethanolamine, 2,2-dimethyl-2-phenyl acetophenone, and 2-methoxy-2-phenyl acetophenone.

The polymerization may also take place in the absence of light. For example, the polymerization can be initiated with a redox system, using techniques known to those of skill in the art. In some cases it is advantageous to polymerize macromers using the redox system of the invention, as radical initiator production occurs at reasonable rates over a wide range of temperatures.

Initiators that can be used in the redox system include, without limitation, peroxides such as acetyl, benzoyl, cumyl and t-butyl; hydroperoxides such as t-butyl and cumyl; peresters such as t-butyl perbenzoate; acyl alkylsulfonyl peroxides, dialkyl peroxydicarbonates, diperoxyketals, ketone peroxide, azo compounds such as 2,2'-azo(bis) isobutyronitrile (AIBN), disulfides, and tetrazenes.

Shaping of Articles

The articles of the present invention may be formed in any shape desired. For example, the articles may be shaped to fit into a specific body cavity. They may also be formed into thin, flat disks or particles, such as microspheres. Alternatively, the articles may be shaped, then processed into the desired shape before use, or ground into fine particles. The desired shape of the article will depend on the specific application.

Macromer particles may be prepared using techniques known in the art, including single and double emulsion solvent evaporation, spray drying, and solvent extraction. As used herein, the term "particles" includes, but is not limited to, microspheres. In a microsphere, a BAS is dispersed throughout the particle. The particles may have a smooth or irregular surface, and may be solid or porous. Methods for making microspheres are described in the literature, for example, in U.S. Pat. No. 4,272,398, Mathiowitz and Langer (J. Controlled Release 5:13–22 (1987)); Mathiowitz et al. (Reactive Polymers 6:275–283 (1987)); Mathiowitz et al. (J. Appl. Polymer Sci. 35:755–774 (1988)); Mathiowitz et al. (Scanning Microscopy 4:329–340 (1990)); Mathiowitz et al. (J. Appl. Polymer Sci., 45:125–134 (1992)); and Benita et al. (J. Pharm. Sci. 73:1721–1724 (1984)), hereby incorporated by reference. In one preferred embodiment of the present invention, the microspheres are formed into hydrogel droplets.

In solvent evaporation, described, for example, in Mathiowitz, et al., (1990), Benita et al. (1984), and U.S. Pat. No. 4,272,398, a polymer is dissolved in a volatile organic solvent, such as methylene chloride. An agent to be incorporated, either in soluble form or dispersed as fine particles, is optionally added to the polymer solution, and the mixture is suspended in an aqueous phase that contains a surface active agent such as poly(vinyl alcohol). The resulting emulsion is stirred until most of the organic solvent evaporates, leaving solid microspheres, which may be washed with water and dried overnight in a lyophilizer.

In solvent removal, as described, for example, by Park et al. (J. Controlled Release 55:181–191 (1998)), a therapeutic or diagnostic agent is dispersed or dissolved in a solution of a selected polymer in a volatile organic solvent such as methylene chloride. The mixture can then be suspended in oil, such as silicon oil, by stirring, to form an emulsion. As the solvent diffuses into the oil phase, the emulsion droplets harden into solid polymer microspheres.

Processes for preparing ultrafine particles of biological molecules by atomizing liquid solutions of the macromolecules, drying the droplets formed in the atomization step, and collecting the particles are described in PCT WO 97/41833, hereby incorporated by reference.

Spray drying is implemented by passing a homogenous mixture of a BAS, such as a therapeutic agent, and the polymerizable macromer used to form a hydrogel through a nozzle, spinning disk, or equivalent device to atomize the mixture to form fine droplets. The substance and the polymerizable macromer may be provided in a solution or suspension, such as an aqueous solution. The fine droplets are exposed to light to cause polymerization of the macromer and formation of the hydrogel droplets incorporating the substance. Hydrogels may be formed according to the methods described in U.S. Pat. No. 5,410,016, hereby incorporated by reference, or other techniques known in the art of polymer chemistry.

In another embodiment, hydrogel particles are prepared by a water-in-oil emulsion process, wherein the polymerizable macromers and the substance to be incorporated are suspended in a water-in-oil emulsion and exposed to light to polymerize the macromers to form hydrogel particles incorporating the substance, such as a BAS. Typically, polymerization may be conducted at room temperature.

The microspheres prepared using the techniques described above are freeze dried, so they have a long shelf life (without biodegradation) and the BAS remains biologically active. Prior to use for injectable formulations, the microspheres are reconstituted in a suitable solution, such as saline or other liquids. For pulmonary delivery, either freeze dried or reconstituted particles may be used.

Properties of the Macromers

The articles of the present invention are biodegradable. Biodegradation occurs at the linkages within the extension oligomers and results in fragments which are non-toxic and easily removed from the body and/or are normal, safe chemical intermediates in the body. These materials are particularly useful for the delivery of hydrophilic materials, since the water soluble regions of the polymer allow water to access the materials trapped within the polymer.

Use of the Macromers

Macromers can be shaped into articles, for example, microspheres, and these articles are capable of degrading under in vivo conditions at rates which permit the controlled release of incorporated substances. Release of such a substance may occur by diffusion of the substance from the polymer prior to degradation and/or by diffusion of the material from the polymer as it degrades. Degradation of the polymer facilitates eventual controlled release of free macromolecules in vivo by gradual hydrolysis of the terminal ester linkages. The burst effects that are sometimes associated with other release systems are thus avoided in a range of formulations.

The rate of release of a BAS depends on many factors, for example, the composition of the water soluble region, the degree of polymerization of the macromer. The rate of release of a BAS also depends on the rate of degradation of the degradable region of the macromer. For example, glycolic esters lead to very rapid degradation, lactic esters to somewhat slower degradation, and caprolactic esters to very slow degradation. When the degradable region consists of polyglycolic acid, the release period is less than one week. When the degradable region consists of poly(lactic acid), the release period is about one week. When the degradable region consists of a copolymer of caprolactone and lactic acid or a copolymer of trimethylene carbonate and lactic acid, the release period is two to four weeks. When the degradable region consists of poly(trimethylene carbonate) or a copolymer of caprolactone and trimethylene carbonate, the release period is about three to eight weeks. When the degradable region consists of poly(trimethylene carbonate) or poly(caprolactone), the release period is longer than about five weeks.

The precise rate of release of a BAS from an article can be further modified by altering the ratio of hydrophilic and hydrophobic components of the article. For example, a very soluble macromer will yield, after polymerization, a hydrophilic gel; hydrophilic hydrogels have been shown to degrade more rapidly than hydrophobic ones. A blend of a hydrophilic macromer (e.g., 4kL5) with a hydrophobic water insoluble macromer (3.4kC6) is used to form a polymerized hydrogel. This hydrogel will have a release rate that is in between the release rate of a hydrogel containing only lactic acid and a hydrogel containing only caprolactone. A macromer in which the degradable region is a copolymer of caprolactone and lactic acid will also have a release rate which is in between the release rate of a hydrogel containing only lactic acid and a hydrogel containing only caprolactone as the primary degradable group. Similarly, hydrophilicity of the active substance also affect the release rate of the BAS, with hydrophilic active substances generally released faster than hydrophobic substances.

The rate of release of a given BAS from a therapeutic article depends on the quantity of the loaded substance, as a percent of the final product formulation. For example, it is generally thought in the polymer field that while a large amount of BAS loading results in a longer period of therapeutic dose delivery, it also results in a large burst effect. Therefore, an article which is loaded with a high amount of a BAS, and which also exhibits a low burst effect would be an optimal article. The articles or the present invention exhibit these characteristics.

Other factors which affect the release rate of a BAS from an article are the aggregation and the solubility of the BAS. In order for the articles of the present invention to have release profiles which are optimal for delivering a BAS, the percent of the BAS which is aggregated should be low. The articles of the present invention contain BAS which are preferably less than 15% aggregated. In preferred embodiments, the articles have this characterization of low aggregation even when they and contain at least 2.5% BAS by dry weight, more preferably at least 5%, and most preferably 20 or 40% by dry weight.

As stated above, another factor which affects the rate of release of a BAS from an article is the solubility of the BAS in the article. In the field of polymer chemistry, it has generally been thought that water-soluble substances, such as a BAS, will yield homogenous systems when incorporated into the macromers of the invention. It has also been thought that substances that do not solubilize in water within the time it takes to form the macromers of the invention will yield heterogenous systems. While the amount of burst in the heterogenous systems can be minimized by using a particulate suspension with small particles, it is generally thought that substances should be in a water soluble format for optimal delivery in a polymer delivery system. The articles of the present invention contain a BAS in an insoluble format, and these articles exhibit a low burst effect, an unexpected result.

Yet another factor that affects the release rate of a BAS from an article is the particle size of the BAS. For example, the articles of the present invention feature a BAS which has been ground and sieved to isolate fine particles which are smaller than approximately 75 microns in any dimension. These particles were used to generate microspheres and the release of the BAS from the microspheres was measured. This release rate was compared to the release rate of the same BAS from the same microspheres, with the exception that the BAS was not fine-ground. The results of these studies indicated that a BAS which is fine-ground results in release rates which are slower and have a low burst effect. By adjusting the factors discussed above, degradation and controlled release may be varied over very wide ranges. For example, release may be designed to occur over hours, days, or months.

The methods of the invention can produce particles that behave as homogenous drug delivery systems. Because of the homogenous nature of the articles of the invention, there is no initial burst of released substance. In addition, the uniform consistency makes it possible to incorporate relatively high amounts of protein, while still minimizing the burst effect.

The present invention also features insoluble macromers. These macromers contain at least one water-soluble region, at least one degradable (e.g., hydrolyzable) region, and at least one polymerizable region. The degradable region contains polymers of glycolic acid, lactic acid, caprolactone, trimethylene carbonate, or blends or copolymers thereof. The degradable region must be water insoluble. For example, a macromer having a degradable region containing 15–20 lactide units can be prepared; this macromer will provide a relatively fast release rate. A macromer with a degradable region containing 6 caprolactone units will provide a relatively slow release rate. A macromer with a degradable region containing a copolymer of 6 caprolactone units, 4 lactide units, and 4 glycolide units will provide a fast release rate, and a macromer with a degradable region containing a copolymer of 3 lactide units and 7 trimethylene carbonate units will provide an intermediate release rate.

The water soluble region of these macromers is preferably PEG. The water soluble region can have multiple arms; for example, it may be star-shaped or comb-shaped, as described, for example in U.S. Pat. No. 5,410,016, incorporated herein by reference. The water soluble region preferably has 3, 4, 6, or 8 arms and a molecular weight of 500 to 20,000, preferably, 1,000 to 10,000 daltons.

Methods for Increasing Protein Precipitation

The articles of the present invention, can be made to contain a BAS in an insoluble format, by combining the BAS with a molecule, or mixture or molecules which preferentially excludes proteins, and a macromer, forming a mixture of these reagents, and polymerizing the mixture. A molecule or mixture of molecules which preferentially exclude proteins can be used in the formation of the article to increase protein precipitation. Examples of molecules which preferentially exclude proteins include, but are not limited to, macromers, poly(ethylene glycol), hyaluronic acid, and poly(vinylpyrrolidone). A reagent which carries a positive or negative ion charge may be used in the formation of the articles of the invention in order to increase the precipitation of the BAS in the mixture which is then polymerized to form the article. The optimal reagent to be used depends on the charge of the protein, which is affected by the pH of the mixture. Examples of mixtures of molecules which preferentially exclude proteins include, but are not limited to, a mixture of molecules comprising a positively charged ion-carrying reagent, for example, triethanolamine or Tris (for example, when the pH is such that the protein is negatively charged); or a mixture of molecules comprising a negatively charged ion-carrying reagent, such as sodium dodecyl sulfate (for example, when the pH is such that the protein is positively charged). A mixture comprising a surfactant, for example, Tween 20, Tween 80, or poloxamer F68, may also be used to increase the precipitation of the protein.

High Load and Low Burst Characteristics

A therapeutic agent, for example, a BAS may be readily incorporated in high yield into the articles described herein. For example, articles may be prepared containing at least 5% active substance by dry weight. Preferably, the articles contain at least 10, 25, or 40% by dry weight.

As discussed above, the BAS of the present invention is in an insoluble format when combined with a macromer and formed into an article. The combination of high load and the insoluble format of the active substance in the article provides the article with a slow release profile, with little initial burst. These results are surprising given the view in the field of polymers that an article containing an insoluble active substance will have large initial burst of the active substance.

The BAS contained in the articles of the present invention is insoluble. The formulation of articles containing an insoluble BAS may be achieved, for example, by mixing the BAS with PEG, and then combining these reagents with the desired macromer.

The amount of BAS loaded into a microsphere may be measured by combining it with a macromer and shaping into articles. The articles may then be placed into an appropriate solvent, for example phosphate buffered release media (0.01% $NaN_3$, 0.05 M PBS, pH 7.4) and assayed for the amount of BAS present by means available in the art, such as spectrophotometry.

Biologically Active Substances

A BAS that can be incorporated into the articles of the invention include therapeutic, diagnostic, and prophylactic agents. They can be naturally occurring compounds, synthetic organic compounds, or inorganic compounds. Substances that can be incorporated into the articles of the invention include proteins, polypeptides, carbohydrates, inorganic materials, antibiotics, antineoplastic agents, local anesthetics, antiangiogenic agents, vasoactive agents, anticoagulants, immunomodulators, cytotoxic agents, antiviral agents, antibodies, neurotransmitters, psychoactive drugs, oligonucleotides, lipids, cells, tissues, tissue or cell aggregates, and combinations thereof.

Exemplary therapeutic agents include growth hormone, for example human growth hormone, calcitonin, granulocyte macrophage colony stimulating factor (GMCSF), ciliary neurotrophic factor, parathyroid hormone, and the cystic fibrosis transmembrane regulator gene. Other specific therapeutic agents include parathyroid hormone-related polypeptide, somatostatin, testosterone, progesterone, estradiol, nicotine, fentanyl, norethisterone, clonidine, scopolomine, salicylate, salmeterol, formeterol, albeterol, and valium.

Drugs for the treatment of pneumonia may be used, including pentamidine isethionate. Drugs for the treatment of pulmonary conditions, such as asthma, may be used, including albuterol sulfate, β-agonists, metaproterenol sulfate, beclomethasone dipropionate, triamcinolone acetamide, budesonide acetonide, ipratropium bromide, flunisolide, cromolyn sodium, ergotamine tartrate, and protein or polypeptide drugs such as TNF antagonists or interleukin antagonists.

Other therapeutic agents include cancer chemotherapeutic agents, such as cytokines, chemokines, lymphokines, and substantially purified nucleic acids, and vaccines, such as attenuated influenza virus. Substantially purified nucleic acids that can be incorporated include genomic nucleic acid sequences, cDNAs encoding proteins, expression vectors, antisense molecules that bind to complementary nucleic acid sequences to inhibit transcription or translation, and ribozymes. For example, genes for the treatment of diseases such as cystic fibrosis can be administered. Polysaccharides, such as heparin, can also be administered.

Other therapeutic agents include tissue plasminogen activator (t-PA), superoxide dismutase, catalase luteinizing hormone releasing hormone (LHRH) antagonists, IL-11 platelet factor, IL-4 receptor, enbrel, IL-1 receptor antagonists, TNF receptor fusion proteins, megakaryocyte growth and development factor (MGDF), stemgen, anti-HER-2 and anti-VEGF humanized monoclonal antibody, anti-Tac antibody, GLP-1 amylin, and GLP-1 amylin analogues.

Additional therapeutic agents include atrial natriuretic factor, atrial natriuretic peptide, beta-human chorionic gonadotropin, basic fibroblast growth factor, bovine growth hormone, bone morphogenetic protein, B cell stimulating factor-1, B cell stimulating factor-2, bovine somatotropin, carcinobreaking factor, cartilage induction factor, corticotropin releasing factor, colony stimulating factor, differentiating factor-1, endothelial cell growth factor, erythroid differentiation factor, elongation factor 1-alpha, epidermal growth factor, erythropoietin, thrombopoietin, thymopoietin, fibroblast growth factor, follicle stimulating hormone, granulocyte colony stimulating factor, glial fibrillary acidic protein, growth hormone releasing factor, human alpha-1 antitrypsin, human atrial natriuretic factor, human chorionic gonadotropin, human leukemia inhibitory factor, hemopoietin-1, hepatocyte growth factor, human transforming growth factor, human thyroid-stimulating hormone, interferon, immunoglobulin A, immunoglobulin D, immunoglobulin E, insulin-like growth factor-1, insulin-like growth factor-II, immunoglobulin G, immunoglobulin M, interleukin-1, interleukin-2, interleukin-3, interleukin-4, interleukin-5, interleukin-6, kidney plasminogen activator, lectin cell adhesion molecule, luteinizing hormone, leukemia inhibitor factor, monoclonal antibody, macrophage activating factor, macrophage cytotoxic factor, macrophage colony stimulating factor, megakaryocyte colony stimulating factor, tumor necrosis factor, macrophage inhibitory factor, Mullerian inhibiting substance, megakaryocyte stimulating factor, melanocyte stimulating factor, neutrophil chemotactic factor, nerve growth factor, novel plasminogen activator, nonsteroidal anti-inflammatory drug, osteogenic factor extract, antitumor lymphokine, prostate-specific antigen, anti-platelet activating factor, plasminogen activator inhibitor, platelet-derived growth factor, platelet-derived wound healing formula, plasmatic human interleukin inducing protein, tumor angiogenesis factor, tissue control factor, T cell growth factor, T cell modulatory peptide, transforming growth factor, tumor growth inhibitor, tumor inhibiting factor, tissue inhibitor of metalloproteinases, tumor necrosis factor, tissue plasminogen activator, thyroid stimulating hormone, urokinase-plasminogen activator, vascular endothelial growth factor, and vasoactive intestinal peptide.

A preferred BAS is a substantially purified polypeptide or protein. Proteins are generally defined as consisting of 100 amino acid residues or more; polypeptides are less than 100 amino acid residues. Unless otherwise stated, the term protein, as used herein, refers to both proteins and polypeptides. The proteins may be produced, for example, by isolation from natural sources or recombinantly. Examples include insulin and other hormones, including growth hormones, such as human growth hormone and bovine growth hormone. Other exemplary proteins include Factor VIII, Factor IX, Factor VIIa, and anti-inflammatory agents, such as interleukins, including interleukin-4. Other exemplary proteins include enzymes, such as DNase and proteases. Other proteins include cytokines, interferons, including interferon alpha and interferon beta, poetins, angiogenic factors, differentiation factors, colony-stimulating factors, growth factors, ceredase, gibberellins, auxins, and vitamins, and fragments thereof. Exemplary growth factors include vascular endothelial growth factor (VEGF), endothelial cell growth factor (ECGF), basic fibroblast growth factor (bFGF), and platelet derived growth factor (PDGF).

Proteins are stable in the hydrogels of the present invention. For example, many of the proteins are protected from dimerization or aggregation, as discussed below in the Examples. The enzymatic degradation of proteins or polypeptides can be further minimized by co-incorporating peptidase-inhibitors.

Treatment of an Animal Using Slow Release Protein Polymers

The polymer articles of the present invention may be used to treat an animal, for example, a mouse, rat, or human, by delivering a BAS to the animal. The articles may contain such a BAS as any of those described above. Various routes of administration may be used to deliver the articles of the present invention, as described below.

The results of the treatment of an animal with therapeutic articles containing a BAS, as described herein, will vary according to the BAS being delivered. For example, if hGH is delivered through the therapeutic articles of the present invention, one would expect to observe an increase in growth as a result of such a treatment. If erythropoietin is delivered through the therapeutic articles, one would expect to observe an increase in reticulocytes in the animal as a result of the treatment. If insulin is delivered through the therapeutic articles, then the treatment should result in a decrease in blood glucose levels.

The articles of the present invention provide optimal delivery of a BAS, because they release the BAS in a controlled manner with a low burst effect. The result of such a delivery rate is that the drug is delivered steadily over a desired period of time. A slower and steadier rate of delivery may in turn result in a reduction in the frequency with which the BAS must be administered to the animal. In addition, a low burst effect may be highly desirable in some circumstances where the delivery of too much BAS to a site is deleterious to the animal.

Routes of Administration of the Articles Inhalation

The use of the hydrogel particles of the invention can enhance the delivery of drugs to the lung. Administration to the lung provides for the delivery of drugs that can be transported across the lung tissue barriers and into circulation, as described WO 99/03454.

A problem with the delivery of active substances to the lung is that pulmonary macrophages can take up the materials, thus preventing the material from entering into systemic and local circulation. Uptake occurs when proteins adsorbed to the particles' surfaces bind with receptors on the surfaces of the macrophages. To prevent uptake, the invention provides nonionic hydrogels, e.g., formed with polymers based on polyethylene glycol. These hydrogels adsorb low levels of proteins and thus bind poorly to cell surfaces. Anionic hydrogels, e.g., formed with polyacrylic acid, also adsorb relatively low levels of proteins and thus bind poorly to cell surfaces.

In a further embodiment, biocompatible microcapsules may be formed and the surface provided with water soluble non-ionic polymers such as polyethylene oxide (PEO), to create resistance to cell adhesion, as described in U.S. Pat. No. 5,380,536, hereby incorporated by reference.

The size and density of the particles can also be selected to maximize the quantity of BAS that is delivered to the lung. For example, the macrophages will not take up large particles as efficiently as they will take up small particles. However, large particles are not delivered to the deep lung as well as small particles are. To overcome these conflicting factors, the invention provides small particles that can swell as they hydrate. The particles are administered to the deep lung as small (i.e., 1–5 microns), dry, or slightly wet, particles; upon hydration, they swell, and therefore become resistant to uptake by the pulmonary macrophages. The swelling can occur when the particles are hydrated from the dry state and when they are hydrated from one state of hydration to another by a change in temperature, pH, salt concentration, or the presence of other solvents, for example, depending upon the chemical and physical nature of the hydrogel polymer.

As used herein, the term "dry" means that the particles of the powder have a moisture content such that the powder is readily dispersible in an inhalation device to form an aerosol. Preferably, the moisture content of the particles is below 10% by weight water, more preferably below about 5%, or optionally below about 2%, or lower.

The density of the particles is expressed in terms of tap density. Tap density is a standard measure of the envelope mass density. The envelope mass density of an isotropic particle is defined as the mass of the particle divided by the minimum sphere envelope volume within which it can be enclosed. The density of particles can be measured using a GeoPyc (Micrometers Instrument Corp., Norcross, Ga.) or a AutoTap (Quantachrome Corp., Boyton Beach, Fla.).

For example, the density of 3.4kL5 particles was determined as follows. 3.4kL5 (1.0025 g), 200 mM TEOA in PBS; pH 7 (1.0260 g), and 1000 ppm Eosin (0.1028 g) were combined. 200 mg of this solution was mixed with talc (0.1015 g). The resulting suspension was placed in a 100 μl glass pipet and polymerized by light for 15 seconds (ILC Technology, Inc. Xenon Light Source with Fiber Optics). The rod was pushed out, placed on aluminum foil, and further polymerized for 3.5 minutes. The hardened rod was lyophilized (vacuum 15E-3 mbar, trap temp. −50° C.) for 18 hours. The dry rod (water content <10%) was cut into small pieces, placed in heptane, and minced using a homogenizer (Silverson L4RT-A) at 5,000 rpm to small particles. The wet particles were air-dried, followed by nitrogen gas flow. The particles sizes ranged from 1 micron to 0.5 mm.

1.645 g of these particles was placed in a 10 mL graduated cylinder. The graduated cylinder was mounted on top of an Autotap densimeter (Quantachrome). The sample was tapped 100 times and the particles' volume was read. The process was repeated until no change in volume was observed. The final volume was 2.8 ml. The tap density of the particles was 1.6435 g/2.8 ml 0.5870 g/ml.

In addition to particles, the polymer may be provided in other shapes suitable for delivery to the deep lung. For example, PEG emulsion microspheres are subjected to high pressure and a vacuum onto a flat plate to form very light very thin layers, for example, having a snow flake consistency, that react differently to fluidic wind forces. The resulting thin flakes can be, e.g., 0.01 micron, 1 micron, or 10 microns thick.

The particles can be administered to the respiratory system alone, or in any appropriate pharmaceutically acceptable excipient, such as a liquid, for example, saline, or a powder. Aerosol dosages, formulations and delivery systems may be selected for a particular therapeutic application, as described, for example, in Gonda ("Aerosols for delivery of therapeutic and diagnostic agents to the respiratory tract," in Critical Reviews in Therapeutic Drug Carrier Systems, 6:273–313, 1990); and in Moren ("Aerosol dosage forms and formulations," in: Aerosols in Medicine. Principles, Diagnosis and Therapy, Moren, et al., Eds., Elsevier, Amsterdam, 1985).

Pulmonary drug delivery may be achieved using devices such as liquid nebulizers, aerosol-based metered dose inhalers, and dry powder dispersion devices. For the use of dry powder dispersion devices, the polymer particle incorporating the therapeutic agent is formulated as a dry powder, for example, by lyophilization or spray-drying. Methods for preparing spray-dried, pharmaceutical-based dry powders including a pharmaceutically acceptable amount of a therapeutic agent and a carrier are described in PCT WO 96/32149, hereby incorporated by reference.

Examples of a BAS that can be administered to the lung include, without limitation, insulin, antitrypsin, calcitonin, alpha interferon, beta interferon, GLP-1, and DNAse.

Nasal Delivery

The articles of the present invention can also be used to administer compounds nasally. For example, a vaccine containing freeze dried or reconstituted microspheres can be administered nasally.

Intramuscular and Subcutaneous Administration

The articles of the present invention can be used to administer microspheres that degrade over several days to 3 months, by intramuscular injection or by subcutaneous injection.

For example, growth hormone can be administered subcutaneously; the hormone leaves the microspheres at the site of injection as they degrade. Growth hormone enters the systemic circulation, where, in turn, it exerts its effects directly, and indirectly through induction of somatomedin production in the liver and in other tissues. For this application, particle sizes of up to 0.5 mm can be used.

In other embodiments, the active agent is a vaccine, such as tetanus vaccine, other proteins or polypeptides, or more complex immunogens. The vaccine is released over time, from one week to many weeks, resulting in an improved immune response to the vaccine, compared to a bolus injection followed by one or more booster shots with the same total dose of immunogen. Mixtures of different types of microspheres can result in initial and booster shot-type immunization as well.

Intravenous Administration

Articles that contain a BAS useful in treating clotting disorders, such as Factor VIII or Factor IX for hemophilia, can be administered by intravenous injection. The BAS is released over days to weeks. A therapeutic level of the BAS is maintained that results in a better clinical outcome. In addition, potentially lower total doses of a BAS can be administered, with a corresponding economic benefit. These approaches help promote patient compliance.

In the case of intravenous injection, it is important to formulate the microspheres in acceptable agents so the microspheres do not aggregate and clog blood vessels. The microspheres must be appropriately sized, so that they don't lodge in capillaries. For this application, particle sizes of 0.2–0.5 microns are preferred.

In a number of inflammatory conditions, as part of the inflammatory process that is mediated by selectin and ICAM expression/binding with neutrophil intravisation, blood vessels become leaky at the site of inflammation. Hydrogel microspheres may be administered; these microspheres will leak out of blood vessels at the site of inflammation, and then release their BAS payload locally over a period of time. Disease conditions where this approach may be useful could include, but are not limited to, inflammatory bowel diseases, asthma, rheumatoid arthritis, osteoarthritis, emphysema, and cystic fibrosis (with DNase as the enzymatic drug).

Hydrogel microspheres that contain cytokines, lymphokines, or other compounds to treat cancer can be administered by intravenous injection. Blood vessels within large solid tumors are generally leaky, and the blood flow within them is often slow. Thus, microspheres could lodge within solid tumors and release their anticancer BAS locally, either killing tumor cells directly or by activating the immune system locally. This approach could be used, for example, with compounds such as interleukin 2, where the systemic and local toxicity has been dose limiting and where the resulting side effects are significant.

The microspheres of the present invention may be cleared relatively slowly from the circulation. Alternatively, the microspheres can be targeted to exit the circulatory system through leaky blood vessels or through more active targeting mechanisms, e.g., receptor mediated targeting mechanisms.

Oral Administration

In some portions of the gastrointestinal tract, there is relatively good transport of proteins across the intestinal mucosa into the systemic and local circulation. The compositions of the invention, for example, freeze dried microspheres containing protein (with very small particle sizes), can therefore be administered orally in an appropriate enteric formulation that protects the drug-containing microspheres from enzymatic attack and the low pH found in the upper GI tract. Such an enteric formulation could also be designed using several available technologies to gradually expel BAS-containing microspheres as the enteric capsule traverses the gastrointestinal tract. This is described in more detail in WO 99/03454 and in Mathiowitz et al. (Nature 386: 410–414 (1997)). It is anticipated that this approach will have a number of advantages over other approaches for delivering proteins and other molecules, even small molecules, orally. First, PEG and proteins are compatible, so the major manufacturing and stability problems found with other drug delivery approaches can be avoided. Secondly, dried hydrogels are very adhesive to wet tissue. The microparticles will bind well to the GI tract and will be transported into the system via the gastrointestinal circulation or release their contents on the intestinal mucosa; in turn, the drug will enter the systemic and gastrointestinal circulation. Chemical enhancers, or formulations containing compositions that utilize specific and non-specific biological transport mechanisms to facilitate transport across the GI tract into the systemic circulation, can be included as well.

Targeting

Targeting ligands can be attached to the particles via reactive functional groups on the particles. Targeting ligands permit binding interactions of the particle with specific receptor sites, such as those within the lungs or those on endothelial cells specific to different regions in the body's microvasculature. A targeting ligand is selected which specifically or non-specifically binds to particular targets. Exemplary targeting ligands include antibodies and fragments thereof including antibody variable regions, lectins, hormones, or other organic molecules capable of specific binding to receptors on the surfaces of the target cells. Other ligands are described in Science (279:323–324 (1998)), hereby incorporated by reference.

Microspheres can be made with both a BAS and a targeting molecule. Double microspheres can also be made, in which the inner sphere contains drug and the outer PEG shell contains the targeting molecule or reagent.

Excipients and Carriers

The particles incorporating a therapeutic agent or diagnostic agent may be provided in combination with one or more pharmaceutically acceptable excipients available in the art, as described, for example, in PCT WO 95/31479, hereby incorporated by reference. Excipients may be selected that can, in some applications, enhance stability, dispersability, consistency, and bulking to ensure uniform pulmonary delivery. The excipient may be, e.g., human serum albumin (HSA), bulking agents such as carbohydrates, amino acids, polypeptides, pH adjusters or buffers, and salts. Additional excipients include zinc, ascorbic acid, mannitol, sucrose, trehalose, cyclodextrans, polyethylene glycol, and other commonly used pharmaceutical excipients, including those described in The United States Pharmacopeia, published by the United States Pharmacopeia Convention, Inc., 1995 (see, e.g., pp. 2205–2207). Exemplary carbohydrates include monosaccharides, such as galactose, and disaccharides such as lactose. Excipients that stabilize proteins are especially useful.

In some cases, the excipients are used as carriers; i.e., they are used to modulate the release rate of the active substances. For example, mannitol can be used to accelerate or delay release.

There now follow particular examples that describe the preparation of compositions of the invention, and the methods of the invention. These examples are provided for the purpose of illustrating the invention, and should not be construed as limiting.

In some of the following Examples a macromer made of a triad ABA block copolymer of acrylate-PLA-PEG-PLA-acrylate was used. The PEG had a MW of 3,400 daltons; the poly(lactic acids) on both sides had an average of about five lactate units per side; they are therefore referred to herein as "3.4kL5." When a lower molecular weight PEG, such as 2,000 daltons was used, the resulting macromer is abbreviated as "2kL5."

In other Examples an acrylate-PCL-PEG-PCL-acrylate macromer was used. The PEG had a MW of 3,400 daltons and had polycaprolactone on both sides, with an average of about 6 caproyl units per side. The polymer is referred to herein as "3.4kC6."

In yet other Examples a 3-arm macromer was used. This macromer consisted of a PEG core with 3 arms, 3 lactate groups attached to each arm of the PEG. The PEG had a MW of 4,200 daltons and the polymer is referred to herein as "4.2kL3-A3."

EXAMPLE 1
General Preparation of a Macromer Solution

The protein was weighed out, and the following components were added to the protein: (i) 90 mM TEOA/PBS, pH 8.0; (ii) 35% n-vinyl pyrrolidinone (n-VP); and (iii) 1000 ppm Eosin. The resulting mixture was stirred well using a spatula. The solution was kept in the dark for about 10 minutes, or until the macromer had absorbed all of the solution, or until the solution was homogenous.

Macromer solutions having the following ingredients were prepared.

| Amount Protein | Amount 90 mN TEOA | Amount 35% N-VP | Amount 1000 ppm Eosin | Amount 3.4 kL5 | Amount 2 kL5 | Total amount |
|---|---|---|---|---|---|---|
| 15 mg | 57 mg | 15 mg | 3 mg | 45 mg | 0 mg | 135 mg |
| 15 mg | 57 mg | 15 mg | 3 mg | 0 mg | 45 mg | 135 mg |

EXAMPLE 2
Precipitation of hGH and Formulating into Hydrogel Microspheres

To a 100 mg/ml hGH solution in 5 mM ammonium hydrogen carbonate buffer 77 $\mu$l of a 1300 mM triethanolamine, pH 8, solution was added. Upon the addition of 400 mg of PEG 2K to the above solution, a fine precipitate of hGH was formed. The sample was centrifuged at 4000 rpm for several minutes and 0.9 ml of the supernatant was removed. To the precipitated mixture, 1 g of 4.2kL5-A3 macromer was added, followed by the addition of 0.1 ml of a 10 mM Eosin Y solution. The mixture was then emulsified in an oil phase to form microspheres which were polymerized using an argon laser. The in vitro release characteristics of this formulation are shown in FIG. 1. No burst was observed and release continued for at least 5 days.

EXAMPLE 3

Figure 2:
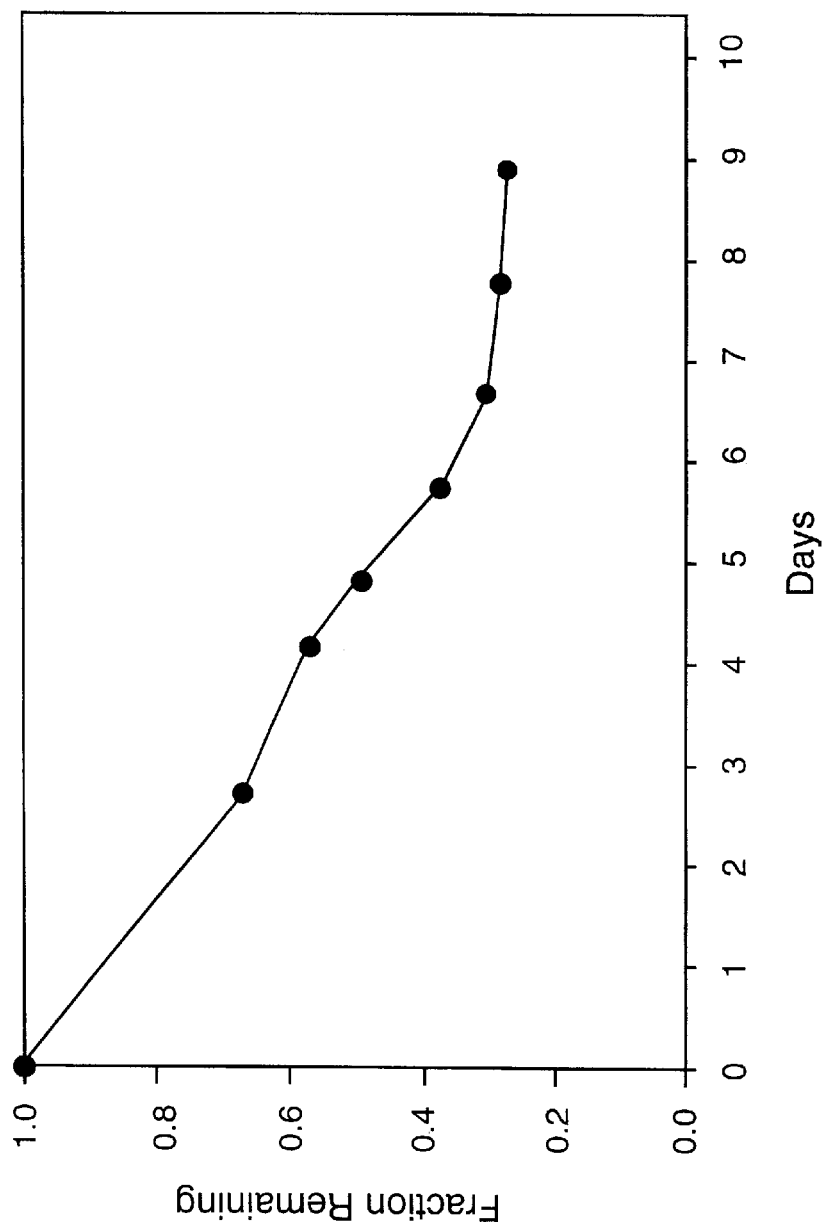
FIG. 2 is the release profile of hGH from 2kL5 microspheres.

Micronization of Freeze-dried Human Growth Hormone and Formulation into Hydrogel Microspheres A 10 mg/ml solution of hGH ammonium acetate was frozen and freeze-dried, resulting in a dry cake of pure hGH. The following macromer solution was prepared: 1 g 2kL5, 1.2 g phosphate buffered saline (pH 7), 0.4 g of a solution of 25% trehalose and 0.4% F-68 in water, 0.24 g of a 10% solution of 2,2-dimethoxy 2 phenyl-acetophenone in tetrahydrofuran. To this solution was added 0.2 g of the freeze-dried hGH. Following mixing to disperse the hGH, the hGH in suspension was further micronized by 20 passages through a 1.5 inch 20 g needle. This suspension was then emulsified in an oil phase to form microspheres which were polymerized by exposure to UV light (365 nm) for 3 min. The in vitro release characteristics of this micropheres are shown in FIG. 2.

EXAMPLE 4
Formation of Articles

The microspheres, in the form of a hydrogel, were placed onto a silanized glass slide. Using pieces of plastic sheets with thicknesses of about 0.4±0.2 mm as spacers, another silanized glass slide was placed on top and held firmly in place using binder clips.

A light source (ILC Technology, Inc. Xenon Light Source with Fiber Optics) was adjusted to about a 5-cm distance. The center of the disk was illuminated; both sides of the disk were illuminated for two minutes each, to form an opaque disk.

EXAMPLE 5
Preparation of Articles Containing 4.2kL3-A3 Macromers and bSA

To 1 ml of 50% ethanol/water solvent, 1 g of 4.2kL3-A3 macromer was added with 7.8 mg of 2,2-dimethoxy-2-phenyl-acetophenone (DMPA). On complete dissolution of the macromer and DMPA, 250 mg of spray dried bSA was added and stirred until the mixture was uniform. The entire mixture was then emulsified in 200 g of a 0.5% lecithin in heavy white mineral oil solution stirred at 600 rpm. Shortly afterwards, the dispersed droplets were photo-polymerized using a Black-Ray B100AP UV lamp for a period of 15 minutes. The in vitro release profile of this formulation, shown in FIG. 3. indicates no burst.

A degradable macromer (4.2kL3-A3) was combined with bSA. The protein was loaded at a loading of 20%, based on dry weight. An emulsion was formed using white heavy mineral oil. Polymerization of the macromer into a hydrogel then occurred through spray drying and UV polymerization techniques.

EXAMPLE 6
Analyses of Biological Active Substance Release from a Macromer

After formation of the articles, as described, for example, in Example 4, the disks were removed and weighed on a clean, tared silanized glass slide. The disk was placed into a heat-sealed membrane bag, as described in more detail below. One 20 $\mu$l disk was placed in each bag. The bag was heat-sealed, placed in 2.0 ml of phosphate buffer release media (0.01% NaN$_3$, 0.05 M PBS; pH 7.4), placed on an orbital shaker turning at 100 rpm, and incubated at 39° C.

For each time point, the bag was placed into fresh 2.0 ml of PBS Release Media. Samples were collected for analysis every day for as long as the BAS was being released.

Membrane bags were prepared as follows. Membrane sheets were cut into pieces of approximately 7±2.5 cm. The sheets were folded in half. Using a Bunsen burner or a propane torch, a spatula was heated until it became red. The edges of the sheets were aligned, and the side of the membrane was cut with the red-hot tweezer to seal the sides. Once the disk was placed into the bag, the last side was sealed using the same heat-sealing technique.

The samples were analyzed daily by SEC-HPLC. Monomers, dimers, and soluble aggregates could be detected using this method. The mobile phase used was 0.08 M TFA in 60/40% CH$_3$CN/H$_2$O, adjusted to pH 2.0, isocratic, with a flow rate of 1.5 ml/min. The signals were detection at a wavelength of 220 nm. The column used was a Bio-Rad Bio-Sil® SEC 250, 5 micron particle size, 300× 7.8 mm ID, equipped with a guard column (Bio-Rad Bio- Sil® SEC 250 Guard, 5 micron particle size, 80×7.8 mm ID). The injection volume was 10 µl. The standard calibration curves were 0, 0.1, 0.25, 0.5, 0.75, and 1 mg/ml bST in the mobile phase.

Figure 3:
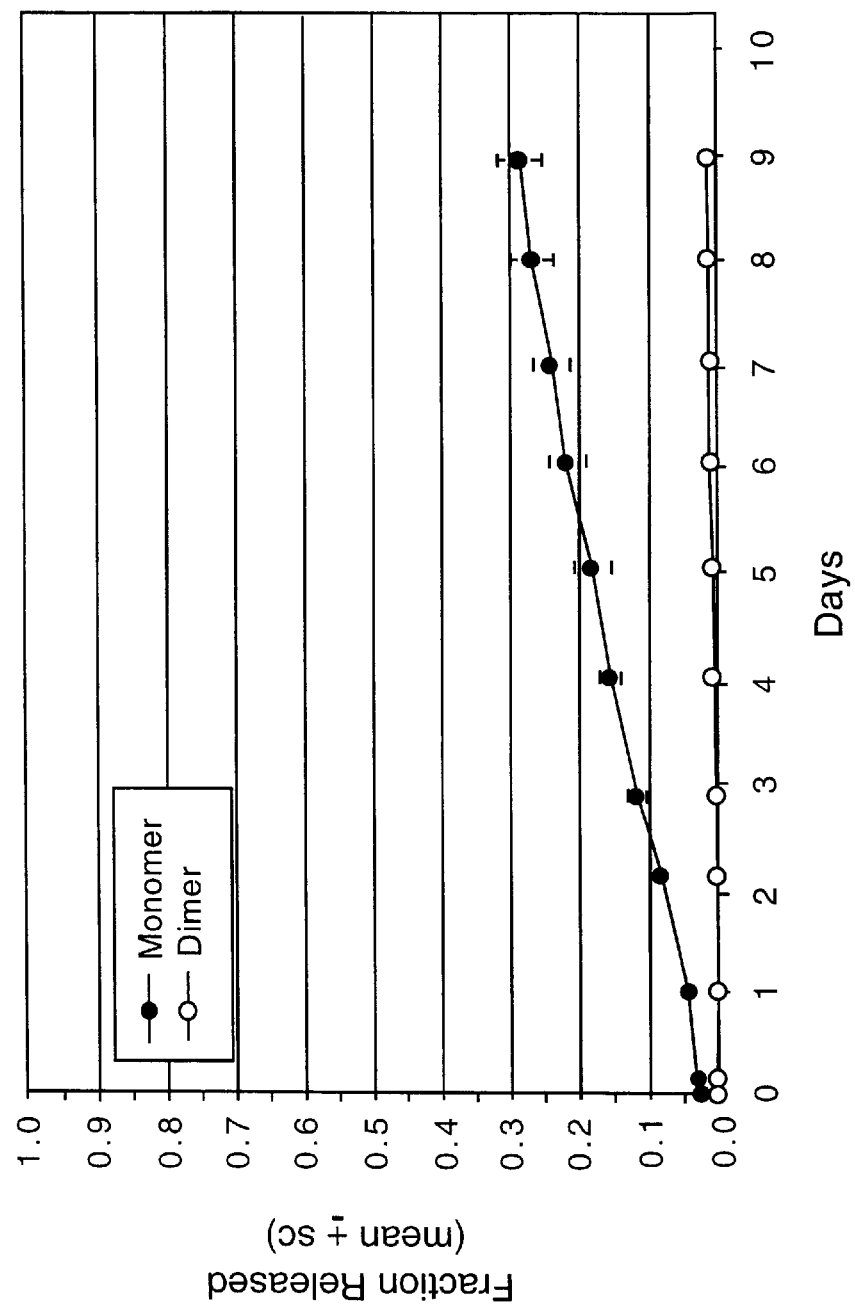
FIG. 3 is a graph depicting the release of spray-dried bSA from 4.2kL3-A3 microspheres.

EXAMPLE 7
Production of Microspheres with Efficient Protein Loading and Low Burst Effects FIG. 3 shows an example of the high protein loading and low burst characteristics of the therapeutic articles of the present invention. The articles contain 4.2kL3-A3 macromers combined with bSA (in either a monomer or dimer form) and formed into microspheres using spray drying techniques. The bSA was loaded at a calculated loading of 20%. Release of bSA from the microspheres was assayed as described above. The release occurred at a slow steady rate, and no burst effect was exhibited. After a period of 9 days, less than 30% of the bSA was released from macromers containing bSA. These results demonstrate that the therapeutic articles of the present invention can provide slow release of a BAS, with little or no burst effect.

EXAMPLE 8
Effect of the Particle Size of a BAS on Release of bSA from 30% 3.4kL5

Figure 4:
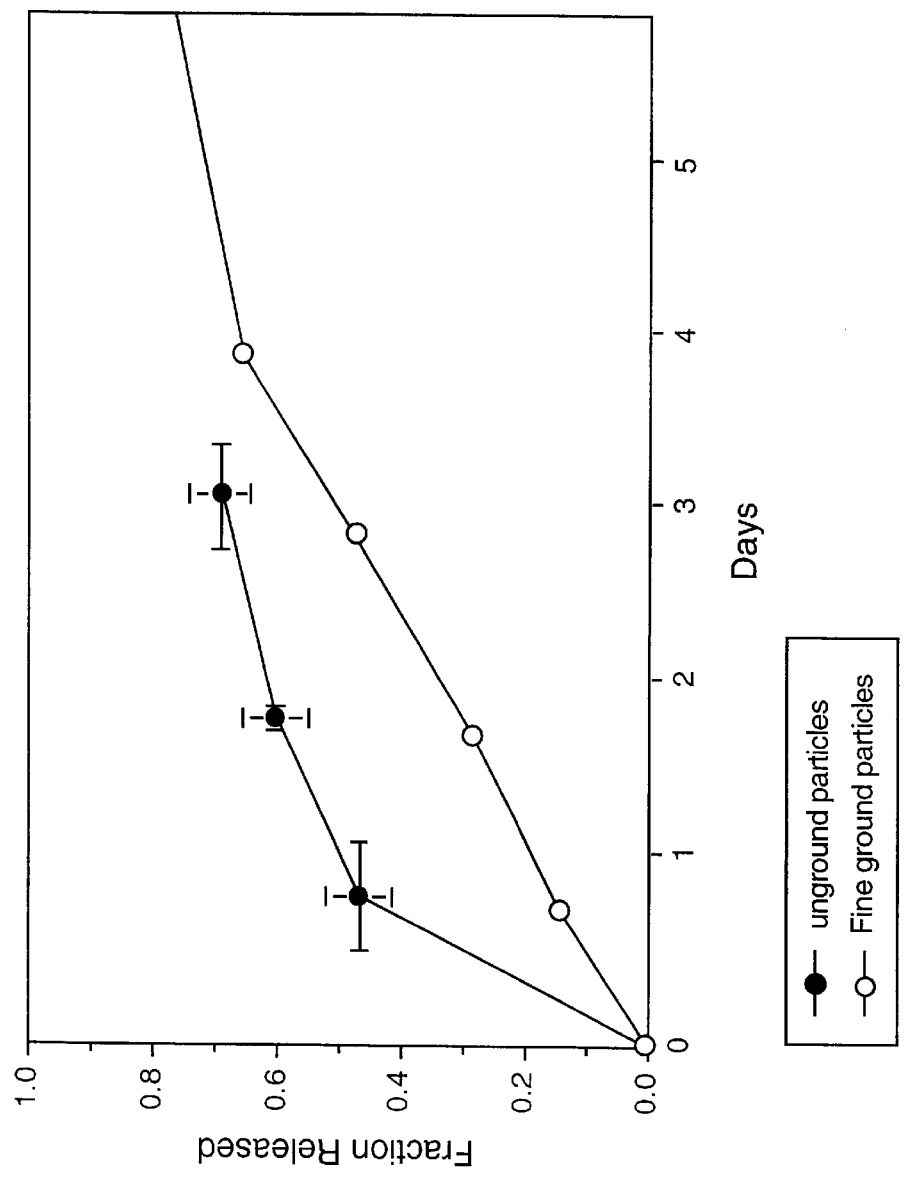
FIG. 4 is a graph of the effects of biologically active particle size on the release of bovine serum albumen (bSA) from 30% 3.4kL5.

The effect of the particle size of a BAS on its release from an article, for example, a microsphere was also determined. The bSA used to form the microspheres was either ground under liquid nitrogen into fine particles of less than approximately 75 microns, or were left unground. Microspheres containing 30% 3.4kL5 and either the fine-ground or unground bSA were formed using the methods described above, and were assayed for the release of bSA, loaded at 25%, based on dry weight. FIG. 4 illustrates the results of these studies. Compared to the microspheres containing unground bSA, the microspheres containing fine-ground bSA released its bSA over a longer period of time. In addition, the microspheres containing the fine-ground bSA exhibited steady rate of release (releasing less than 20% of the total bSA loaded within the first 24 hours), with no burst effect, while the microspheres containing the unground bSA exhibited a burst effect (releasing approximately 50% of the total bSA loaded within 24 hours). These results demonstrate that microspheres containing a BAS which has a small particle size provide slower release profiles and low burst effects.

EXAMPLE 9
Effects of BAS Particle Size and Protein Loading on the Release of Fine-ground bSA (10% Loaded) and Various Crystalline Particles (1–10% Loaded) from 3.4kL5

Figure 5:
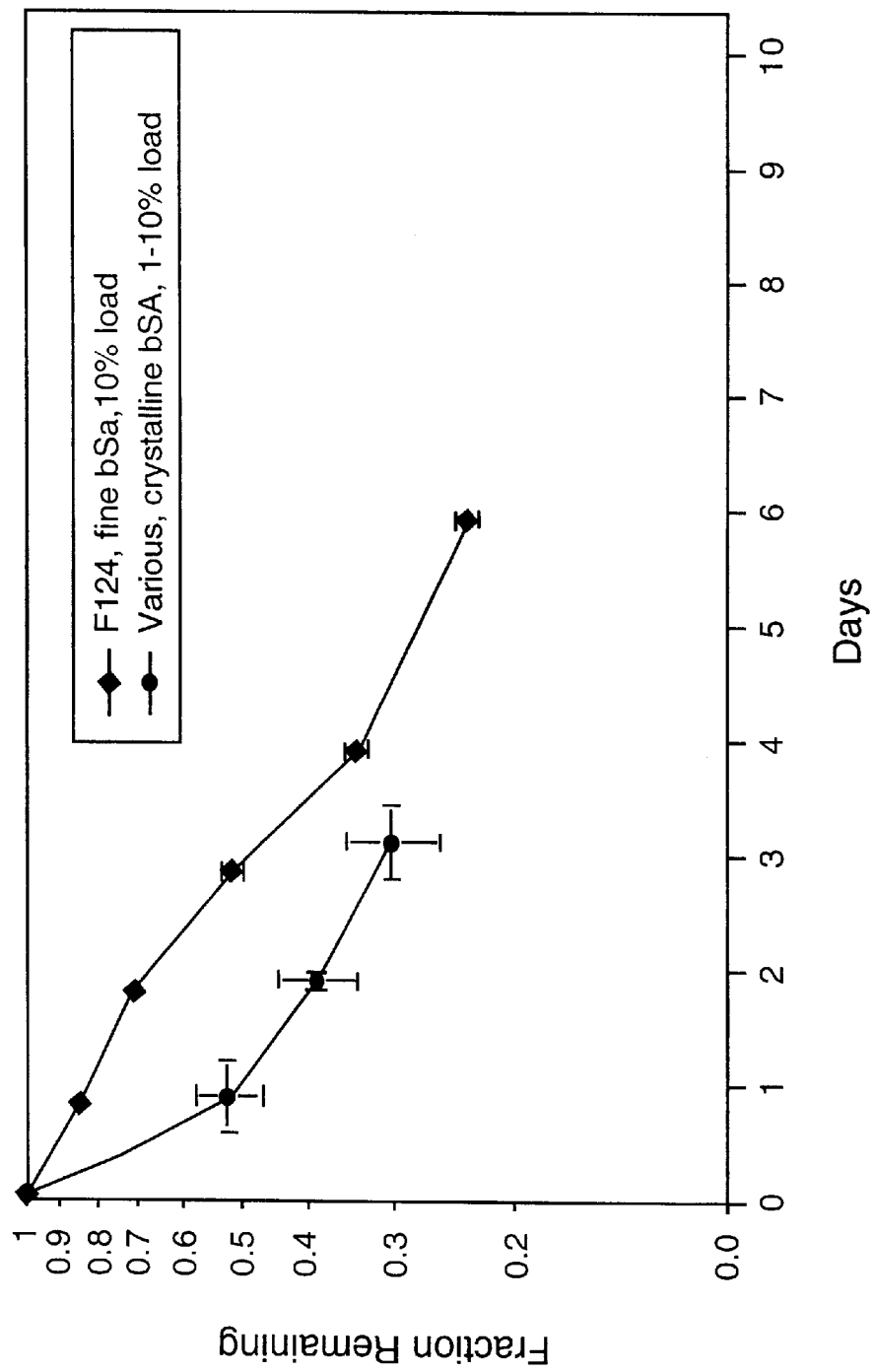
FIG. 5 is a graph of the effect of biologically active particle size and protein loading on the release of fine-ground bSA (10% loaded) and various crystalline particles (1–10% loaded) from 3.4kL5.

The effects of the particle size of a BAS and protein loading on the release of bSA from an article, was also examined (FIG. 5). The bSA used to form the microspheres was either ground under liquid nitrogen into fine particles of less than approximately 75 microns, or were left unground. The fine-ground bSA was combined with 3.4kL5 to form 30% 3.4kL5 microspheres loaded with 10% bSA, using the methods described above. The unground bSA, containing various particle sizes was combined with 3.4kL5 to form 30% 3.4kL5 microspheres loaded with 1–10% bSA. The microspheres were then assayed for the release of bSA. FIG. 5 illustrates the results of these studies. Compared to the microspheres containing unground bSA, the microspheres containing fine-ground bSA, loaded at 10%, released its bSA over a longer period of time. In addition, the microspheres containing the fine-ground bSA exhibited a lower burst effect (releasing approximately 20% of the total bSA loaded within the first 24 hours) than its unground counterpart (releasing almost 50% of the total bSA loaded within the first 24 hours). These results demonstrate that microspheres containing a BAS which has a small particle size and is highly loaded provide a desirable BAS release profile compared to microspheres containing various particle sizes and a lower load of BAS.

EXAMPLE 10
Effect of Protein Particle Size on Release of hGH from 30% 3.4kL5

Figure 6:
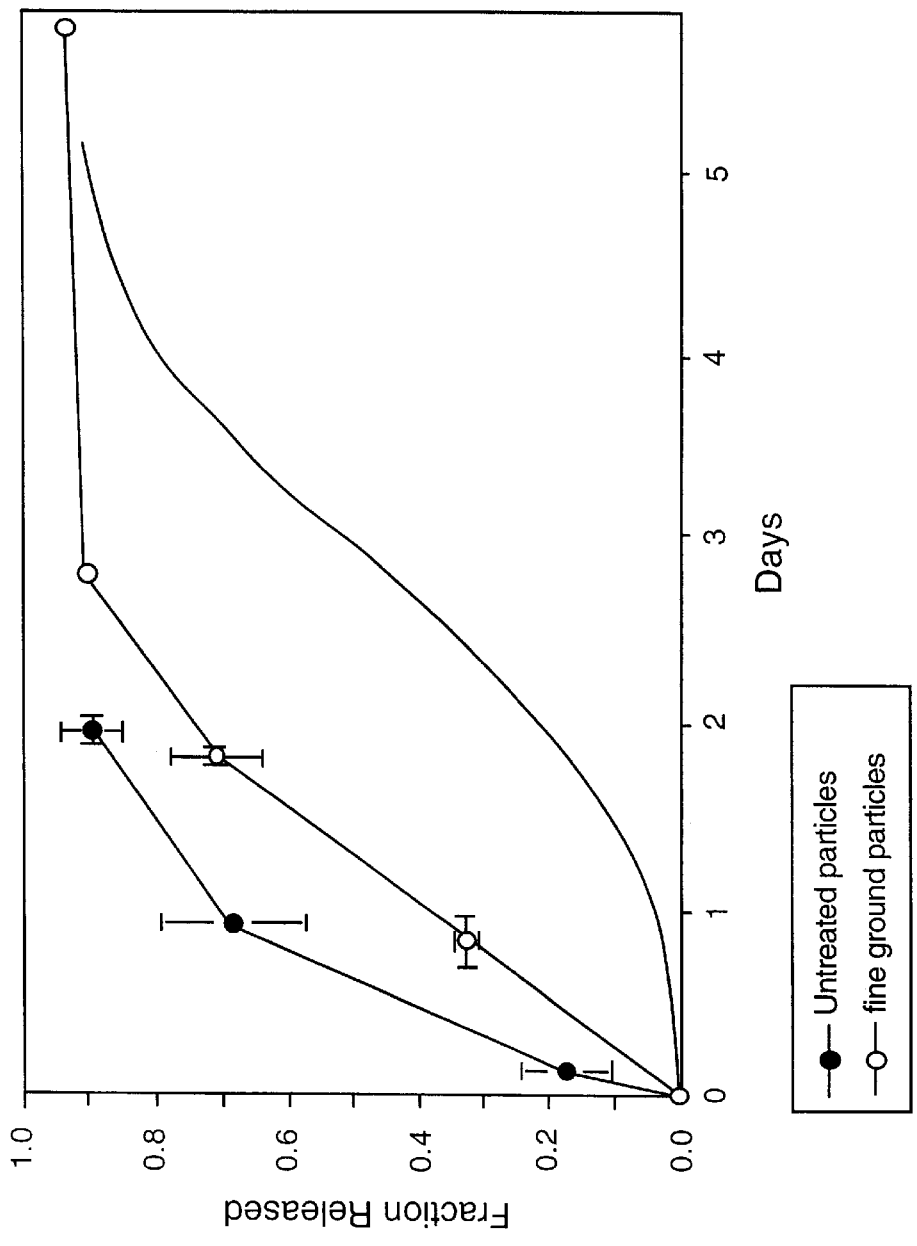
FIG. 6 is a graph of the effects of biologically active particle size on the release of human growth hormone (hGH) from 30% 3.4kL5.

The effect of the particle size of a BAS on its release from microspheres was further examined using microspheres containing either fine-ground or unground hGH. The hGH used to form the microspheres was either ground under liquid nitrogen into fine particles of less than approximately 75 microns, or were left unground. Microspheres containing 30% 3.4kL5 and either the fine-ground or unground hGH were formed using the methods described above, and were assayed for the release of hGH, loaded at 25%, based on dry weight, and 10% as manufacturing conditions. FIG. 6 illustrates the results of these studies. Compared to the microspheres containing unground hGH, the microspheres containing fine-ground hGH released its hGH over a longer period of time. In addition, the microspheres containing the fine-ground hGH exhibited a steady rate of release (releasing less than 40% of the total hGH loaded within the first 24 hours), with no burst effect, while the microspheres containing the unground hGH exhibited a high burst effect (releasing approximately 70% of the total hGH loaded within 24 hours). These results demonstrate that microspheres containing a BAS which has a small particle size provide the characteristics which are highly suitable for delivery of agents for therapeutic use: slow protein release and low burst effects.

EXAMPLE 11
Effect of Microsphere Pore Size on Release of hGH from Macromers

Figure 7:
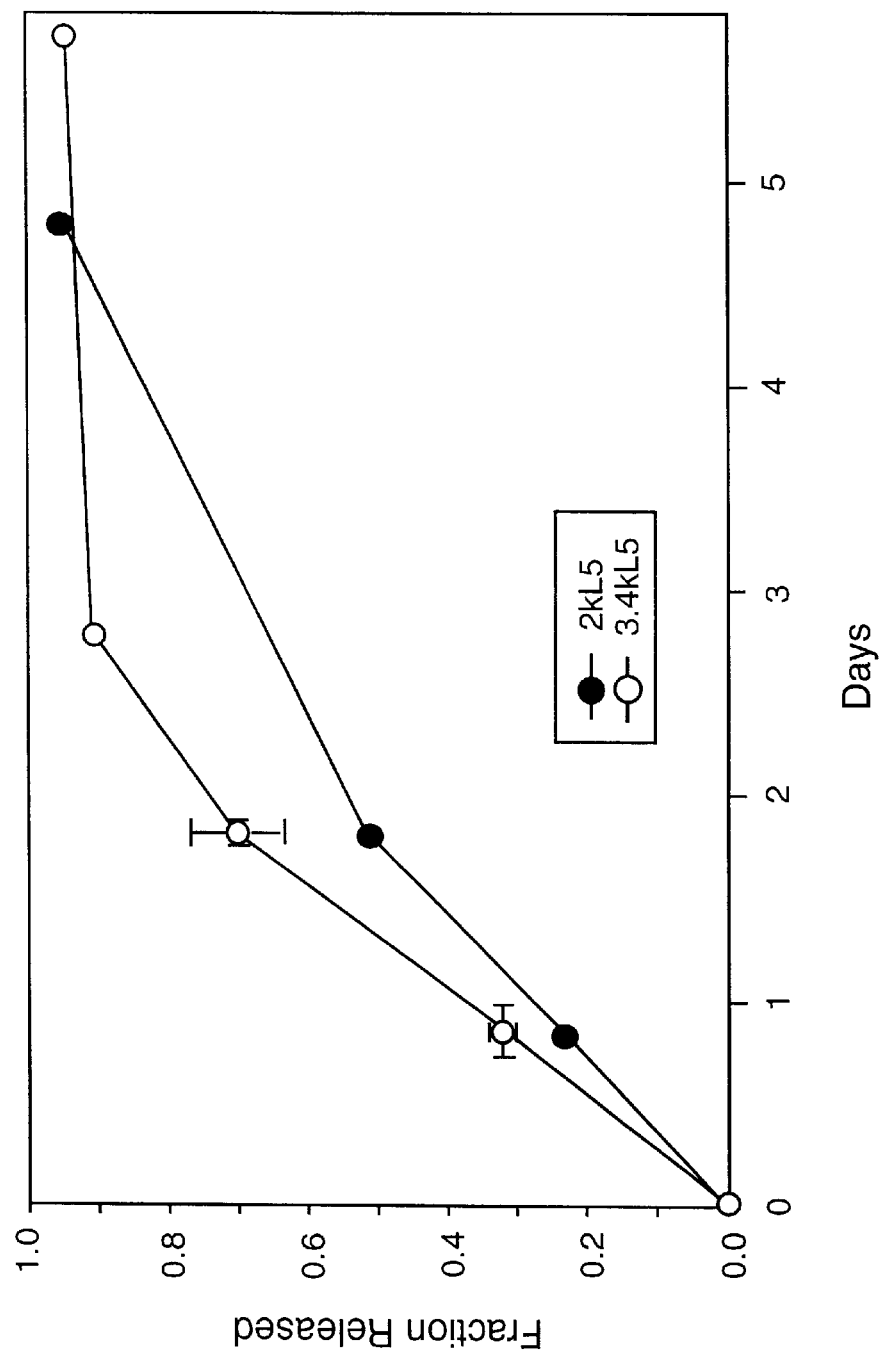
FIG. 7 is a graph of the effect of microsphere pore size on release of micronized hGH from articles.

The effect of the pore size of the microspheres containing fine-ground hGH on the release rate of the hGH was also examined (FIG. 7). Microspheres containing hGH, loaded at 25%, based on dry weight, and 10% as manufacturing conditions, and either 30% 2kL5 or 30% 3.4kL5 were formed using the techniques described above. The microspheres containing 2kL5 had a smaller pore size than the microspheres containing 3.4kL5. The release rate of hGH from these microspheres was then assessed using techniques described above. These studies showed that fine-ground hGH was release from 2kL5-containing microspheres at a slower rate than it was released from 3.4kL5-containing microspheres. These results suggest that macromers which result in a smaller microsphere pore size release a BAS at a slower rate than those which result in a larger microsphere pore size.

EXAMPLE 12
Controlled Release of Bovine Somatotropin in Hypophysectomized Rats The controlled delivery of active bovine somatotropin (MW 20 Kd) was confirmed in the hypophysectomized rat model. Hypophysectomized female rats were purchased from Taconic Labs (Germantown, N.Y.). The rats were weighed each morning. Prior to the initiation of the study, the rats were held 7 days to confirm a lack of significant growth. On day 1 of the study the rats were weighed. The rats were then divided into 3 groups of equal mean weights. Group 1 remained untreated and served as a negative control. Group 2 received an implant of bST in a hydrogel made of a blend of 3:1 of 3.4KL5 and poly(ethylene glycol) diacrylate (each device contained 0.9 to 1.1 mg of bST). The rats in Group 3 were injected with 100 µg bST subcutaneously each day for the duration of the study.

At the end of the 12 day treatment period, the rats were analyzed for their growth over the period of treatment. The rats of Groups 1 did not grow significantly, while the rats of Groups 2 and 3 grew at rates faster than Group 1 and approximately equal to one another.

EXAMPLE 13
Controlled Release of Erythropoietin in Rats

The controlled delivery of active human erythropoietin (EPO) was confirmed in male Sprague-Dawley rats purchased from Taconic Labs (Germantown, N.Y.). Hydrogel devices were manufactured to contain 3000 Units of EPO per device. One of these devices was implanted in each of a number of rats (Group 1). Another group of an equal number of rats (Group 2) received a subcutaneous injection of EPO (1000 Units) daily for 3 days. A third group of rats (Group 3) received no treatment.

On day 5 after implantation of the device and the start of the subcutaneous injections, venous blood samples were obtained from each rat and stored in EDTA. The fraction of reticulocytes (immature red blood cells) was determined after staining with Acridine Orange by automated flow cytometry. The rats in Group 1 had 18% reticulocytes, the rats of Group 2 had 15% reticulocytes, and the rats in Group 3 had 4% reticulocytes.

EXAMPLE 14
Controlled Release of Insulin in Diabetic Rats

Sprague-Dawley rats were purchased from Taconic Labs (Germantown, N.Y.). Diabetes was induced by treatment with streptozotocin (65 mg/kg, i.v.) and confirmed 48 hours later by elevation of blood glucose (>300 mg/dl). Following anesthetization of the rat with pentobarbital (35 mg/kg), a catheter was placed in a jugular vein. After a baseline blood sample was taken for the determination of blood glucose concentration, a hydrogel device containing 1 Unit of insulin was implanted subcutaneously. Blood samples were taken at 15, 30, 60, 120, and 180 minutes after implantation of the device and used to determine blood glucose levels.

The blood glucose level of the rat implanted with the hydrogel device decreased, demonstrating that the devices was capable of releasing insulin in its active form.

To test the pulmonary delivery system for insulin-containing hydrogel particles, the neck of the rat was opened with a midline incision and the trachea was exposed by blunt dissection. A slit was cut into the trachea, and a small polyethylene tube was advanced distally into the lung. A small volume of insulin-containing hydrogel microparticles (total dose of 3 Units of insulin) was instilled into the lung and the tube was removed. Blood samples were taken and analyzed as described above for the subcutaneous device.

The blood glucose levels dropped significantly within 30 minutes and remained low (below 150 mg/d1) for at least 180 minutes.

EXAMPLE 15
Controlled Release of Human Growth Hormone in Hypophysectomized Rats The controlled delivery of active human growth hormone (hGH, MW 20 Kd) is confirmed in the hypophysectomized rat model. Hypophysectomized female rats purchased from Taconic Labs (Germantown, N.Y.) are weighed each morning. Prior to the initiation of the study the rats are held 7 days to confirm lack of growth. The rats are divided into 3 groups of equal mean weights. Group 1 remains untreated and serves as a negative control. Group 2 receives an implant of hGH in a hydrogel made of a 3:1 blend of 3.4kL5 and 3.4kC6 (each device containing approximately 1 mg of hGH). The rats in Group 3 are injected with 100 µg hGH subcutaneously each day for the duration of the study.

It is expected that the untreated control group will not grow during the study, and that the rats of Groups 2 and 3, receiving the hGH hydrogel implant and 100 µg hGH injections daily during the study, respectively, will exhibit continued growth.

EXAMPLE 16
Pulmonary Devices Containing Human Growth Hormone (hGH)

To a 20 ml vial are added: 0.2559 g of 200 mM of TEOA (in PBS buffer; pH 7.0), 0.2548 g of 3.4KL5, 0.0206 g of 1000 PPM eosin (in PBS; pH 7.0), and 0.0615 g hGH (Genentech's hGH injectable formulation, purified by a Millipore Centricon™). The resulting mixture is stirred and placed into 10 ml glass tubes. The tubes are exposed to xenon light (ILC Technology, Inc. Xenon Light Source with Fiber Optics) for 10 seconds. The semi-cured hydrogel is pushed out of the glass tube and further polymerized for 3.5 minutes. The cured hydrogel rods are put into 15 ml of heptane and are ground using a homogenizer (Silverson L4RT-A) for 30 seconds at 5000 rpm, followed by 30 seconds at 3000 rpm. The heptane is decanted, and the powder is dried under nitrogen. The powder is used for pulmonary, oral, or subcutaneous sustained delivery of hGH.

EXAMPLE 17
Oral Formulation for Release of Proteins

Using the techniques described above, insulin, human growth hormone, human alpha interferon, or erythropoietin is incorporated into macromer particles. Using cryomilling or other milling procedures known in the art, very small microparticles are produced, preferably of an average size of less than about 500 nanometers. Such nanoparticles are then introduced into the rat GI tract surgically, using catheter infusion into the upper GI tract. The dosing of such nanoparticles is based upon the assumption that about 0.5% of the drug in the nanoparticles will be detectable in the blood of such rats, e.g., by RIA, with the specific pharmacology of each drug taken into account.

In the case of insulin, blood samples are taken at time t=−15, 0, 30, 60, 90, 120, and 180 minutes, and monitored for insulin by RIA and for blood glucose by glucometer (when insulin is being administered, diabetic rats are utilized).

For other drugs, normal rats are used and blood drug levels are measured at these same time points using RIA or ELISA techniques.

In addition to the above procedures, the above drug-containing microspheres can be modified to enhance their absorption in the small intestine, colon, and other appropriate areas of the GI tract. Such modifications can include precipitating lipid bilayers around the microcapsules so they appear as fat-like particles from digested food, linking molecules such as ferritin to the particles, or putting a charged layer on the outside of the microparticles.

EXAMPLE 18
Evaluation by Reverse Phase HPLC

Microspheres were prepared by first adding 0.154 ml of 3M triethanolamine solution at pH 8.0 (TEOA) to approximately 2 ml of 100 mg/ml solution of hGH in ammonium bicarbonate and then mixing well. Next, about 800 mg of solid PEG 2k was added and mixed with a spatula, resulting in a very small amount of precipitated hGH in the solution. Samples were then centrifuged at 4000 rpm for thirty minutes and about 1.8 g of supernatant was removed. About 1 g of macromer (4.4k PEG tris(lactate)$_3$ triacrylate) was added to each centrifuge tube and stirred. Next, about 0.1 to 0.15 mL of TEOA was added, followed by 0.05 mL of 40 mM Eosin Y. The samples were then centrifuged for three minutes at 4000 rpm. Samples were then polymerized by forming a disc upon exposure to light as described in Example 4 or by first making a microemulsion by mixing with oil (PPG 2k) and then exposing to light as described in Example 4.

The resulting microspheres were analyzed by Reverse Phase HPLC (RP-HPLC). Samples were prepared for RP-HPLC by first extracting hGH from the microspheres with NaOH. Briefly, 10 mg of microspheres was added to 1 mL of NaOH(1N)/Tris (50 mM, pH 7.5) (1:9, v/v) solution and incubated at ambient temperature for 5 minutes. 5N HCl was used to titrate the solution to a final pH of 7.5. The sample was then microcentrifuged for 2 minutes and filtered through a 0.45 micron filter. 100 µL of the hGH solution was injected onto a Vydac C-4 column (214TP54) equilibrated and run under isocratic conditions at 0.5 mL/min. employing n-propanol/Tris (50 mM, pH 7.5)(29:71, v/v) as a solvent. Separation was performed at column temperature of 45° C. over 50 minutes with UV detection at 220 nm. hGH eluted at a retention time of 33±3 minutes. Results are shown in Table I. The term "% RP" refers to the percentage of protein (hGH) that is not found in the monomer peak, which may include forms of hGH that are normally found in commercially marketed hGH preparations and that are active and safe, such as oxidized and deamidated forms.

TABLE I

| Sample No. | % RP |
|---|---|
| 18-86-1 | 41 |
| 318-1 | 48 |
| 318-2 | 43 |

Other batches of microspheres were prepared by first adding 0.154 ml of 3M Tris buffer at pH 6.0 to about 2 ml of 100 mg/ml hGH solution in ammonium bicarbonate and mixing well. To this solution, about 800 mg of PEG 10k was added as solid to obtain precipitated protein. Samples were then centrifuged at 4000 rpm for thirty minutes and about 1.8 g of supernatant was removed. About 1 g of macromer (4.4 k PEG tris(lactate)$_3$ triacrylate) was added to each centrifuge tube and stirred. Next, about 0.1 to 0.15 mL of TEOA was added, followed by 0.05 mL of 40 mM Eosin Y. The samples were then centrifuged for three minutes at 4000 rpm. Samples were then polymerized by forming a disc upon exposure to light as described in Example 4 or by first making a microemulsion by mixing with oil (PPG 2k) and then exposing to light as described in Example 4. One sample, Sample No. 27-50, was prepared using PEG 20k.

The resulting microspheres were analyzed by Reverse Phase HPLC. Samples were prepared for RP-HPLC either by the NaOH extraction method described above or by the following cryogrinding method. Results are shown in Table II, with the sample preparation method indicated. Approximately 10 mg of microsphere sample was weighed in a microcentrifuge tube. A pestle was placed in the tube and then the tube was immersed in a liquid nitrogen bath for approximately one minute. With the tube still in the liquid nitrogen bath, the sample was ground for approximately five minutes. The tube was then removed and allowed to stand for approximately two minutes at ambient temperature. The ground sample was then suspended in about 1 mL of 25 mM potassium phosphate buffer, pH 6.5. The pestle was removed, and the sample incubated for about ten minutes at ambient temperature. The sample was then centrifuged at 15000 rpm for about five minutes to obtain a clear aqueous phase. The supernatant was the filtered through a 0.45 micron filter. RP-HPLC was performed by injecting 100 µL of sample onto a Vydac C-18 column (218TP54) equilibrated and run under isocratic conditions at 1 mL/min, using n-propanol/potassium phosphate (25 mM, pH 6.5) (27:73, v/v) as a solvent. Separation was performed at a column temperature of 55° C. over 30 minutes with UV detection at 220 nm.

TABLE II

| Sample No. | % RP |
|---|---|
| 27-32 | 26 (NaOH) |
| 27-50 (Tris, PEG 20 k) | 19 (NaOH) |
| 320-4 | 20 (NaOH) |
| 502 | 15.2 (NaOH) |
| 507 | 17 (NaOH) |
| 508 | 15 (NaOH) |
| 530 | 16 (NaOH) |
| 548 | 10.4 (Cryogrind) |
| 556 | 7.7 (Cryogrind) |
| 557 | 8.7 (Cryogrind) |
| 561 | 8.5 (Cryogrind) |
| 570 | 6.2 (Cryogrind) |
| 575 | 7.2 (Cryogrind) |

By comparison, microspheres made without a molecule that preferentially excludes proteins ("Control" in Table III), yield %RP values of 53% using the NaOH extraction method, and 23% using the cryogrind method. Also presented in Table III is a comparison of the two sample preparation methods.

TABLE III

| Sample No. | % RP NaOH Method | % RP Cryogrind Method |
|---|---|---|
| Control | 53 | 23 |
| 361 | 30.2 | 15 |
| 362 | 28 | 15 |

Other Embodiments

From the foregoing description, it will be apparent that variations and modifications may be made to the invention described herein to adopt it to various usages and conditions. Such embodiments are also within the scope of the following claims.

All publications and patents mentioned in this specification are herein incorporated by reference to the same extent as if each individual publication or patent was specifically and individually indicated to be incorporated by reference.

What is claimed is:

1. A biocompatible therapeutic article comprising, a macromer, a biologically active substance, and a molecule or mixture of molecules which preferentially excludes proteins, wherein said biologically active substance is a protein or a polypeptide and said molecule or mixture of molecules is present in amounts sufficient to reduce the solubility of said biologically active substance in said article to less than 10 mg/ml.

2. The biocompatible therapeutic article of claim 1, wherein said biocompatible therapeutic article has at least one of the following properties: said biologically active substance being less than 15% aggregated; said article containing at least 10% macromer and at least 5% biologically active substance, by dry weight; the time at which 5% of the releasable biologically active substance is released from said article being greater than $\frac{1}{16}$ of $t_{50}$; or $t_{50}$ is greater than or equal to $\frac{5}{8}$ of $t_{80}$.

3. The biocompatible therapeutic article of claim 2, wherein said biocompatible therapeutic article has at least two of said properties.

4. The biocompatible therapeutic article of claim 2, wherein said biocompatible therapeutic article has all of said properties.

5. The biocompatible therapeutic article of claim 1, wherein said molecule which preferentially excludes proteins is selected from the group consisting of a macromer, poly(ethylene glycol), hyaluronic acid, and poly(vinylpyrrolidone).

6. The biocompatible therapeutic article of claim 5, wherein said molecule which preferentially excludes proteins is poly(ethylene glycol).

7. The biocompatible therapeutic article of claim 1, wherein said macromer is a hydrogel.

8. The biocompatible therapeutic article of claim 1, wherein said macromer comprises:
  (a) a region forming a central core;
  (b) at least two degradable regions attached to said core; and
  (c) at least two polymerizable end groups, wherein said polymerizable end groups are attached to said degradable regions.

9. The biocompatible therapeutic article of claim 8, wherein said central core comprises a polymer selected from the group consisting of poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, polysaccharides, carbohydrates, proteins, and combinations thereof.

10. The biocompatible therapeutic article of claim 8, wherein said degradable regions comprise a polymer selected from the group consisting of poly($\alpha$-hydroxy acids), poly(lactones), poly(amino acids), poly(anhydrides), poly(orthoesters), poly(orthocarbonates), and poly(phosphoesters).

11. The biocompatible therapeutic article of claim 10, wherein said poly($\alpha$-hydroxy acid) is selected from the group consisting of poly(glycolic acid), poly(DL-lactic acid), and poly(L-lactic acid).

12. The biocompatible therapeutic article of claim 10, wherein said poly(lactone) is selected from the group consisting of poly($\epsilon$-caprolactone), poly($\delta$-valerolactone), and poly($\gamma$-butyrolactone).

13. The biocompatible therapeutic article of claim 8, wherein said degradable regions comprise poly(caprolactone).

14. The biocompatible therapeutic article of claim 8, wherein said polymerizable end groups contain a carbon—carbon double bond capable of polymerizing said macromer.

15. The biocompatible therapeutic article of claim 8, wherein said macromer comprises:
  (a) a water soluble region comprising three-armed poly(ethylene glycol) with a molecular weight of 3,000 to 6,000 daltons;
  (b) lactate groups attached to the region in (a); and
  (c) acrylate groups capping the region in (b).

16. The biocompatible therapeutic article of claim 8, wherein said macromer is comprises:
  (a) a water soluble region comprising poly(ethylene glycol) with a molecular weight of either 2,000 or 3,400 daltons;
  (b) lactate groups on either side of region in (a); and
  (c) acrylate groups capping either side of the region in (b).

17. The biocompatible therapeutic article of claim 8, wherein said macromer is comprises:
  (a) a water soluble region comprising poly(ethylene glycol) with a molecular weight of 3,400 daltons;
  (b) caprolactone groups on either side of region in (a); and
  (c) acrylate groups capping either side of the region in (b).

18. The biocompatible therapeutic article of claim 2, wherein said article comprises at least 5% active substance by dry weight.

19. The biocompatible therapeutic article of claim 18, wherein said article comprises at least 10% active substance by dry weight.

20. The biocompatible therapeutic article of claim 19, wherein said article comprises at least 30% active substance by dry weight.

21. The biocompatible therapeutic article of claim 1, wherein said article is biodegradable.

22. A method for making a biocompatible therapeutic article comprising the steps of:
  (a) combining said biologically active substance with a molecule or mixture of molecules which preferentially excludes proteins, wherein said biologically active substance is a protein or a polypeptide;
  (b) combining the mixture formed in step (a) with a macromer, wherein said molecule or mixture of molecules is present in amounts sufficient to reduce the solubility of said biologically active substance in the mixture of step (b) to less than 10 mg/ml; and
  (c) forming a mixture of the combination formed in step (b) to form a biocompatible therapeutic article.

23. The method of claim 22 further comprising the step of:
  (d) polymerizing said mixture formed in step (c).

24. The method of claim 22, wherein steps (a) and (b) are combined into a single combination step.

25. The method of claim 22, wherein said biocompatible therapeutic article has at least one of the following properties: said biologically active substance being less than 15% aggregated; said article containing at least 10% macromer and at least 5% biologically active substance, by dry weight; the time at which 5% of the releasable biologically active substance is released from said article being greater than $\frac{1}{16}$ of $t_{50}$; or $t_{50}$ is greater than or equal to $\frac{5}{8}$ of $t_{80}$.

26. The method of claim 25, wherein said biocompatible therapeutic article has at least two of said properties.

27. The method of claim 25, wherein said biocompatible therapeutic article has all of said properties.

28. The method of claim 22, wherein said molecule which preferentially excludes proteins is selected from the group consisting of a macromer, poly(ethylene glycol), hyaluronic acid, and poly(vinylpyrrolidone).

29. The method of claim 22, wherein said molecule which preferentially excludes proteins is poly(ethylene glycol).

30. The method of claim 22, wherein said macromer is a hydrogel.

31. The method of claim 22, wherein said therapeutic article comprises at least 5% active substance by dry weight.

32. The method of claim 31, wherein said therapeutic article comprises at least 10% active substance by dry weight.

33. The method of claim 32, wherein said therapeutic article comprises at least 30% active substance by dry weight.

34. A method of treating an animal, said method comprising administering the biocompatible therapeutic article of claim 1 to a mammal.

35. The method of claim 34, wherein said mammal is a rodent.

36. The method of claim 34, wherein said mammal is a human.

37. The method of claim 22 or 34, wherein said macromer comprises:

(a) a water soluble region forming a central core;

(b) at least two degradable regions attached to said core; and (c) at least two polymerizable end groups, wherein said polymerizable end groups are attached to said degradable regions.

38. The method of claim 37, wherein said water soluble region comprises a polymer selected from the group consisting of poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, polysaccharides, carbohydrates, proteins, and combinations thereof.

39. The method of claim 37, wherein said degradable region comprises a polymer selected from the group consisting of poly($\alpha$-hydroxy acids), poly(lactones), poly(amino acids), poly(anhydrides), poly(orthoesters), poly(orthocarbonates), and poly(phosphoesters).

40. The method of claim 39, wherein said poly($\alpha$-hydroxy acid) is selected from the group consisting of poly(glycolic acid), poly(DL-lactic acid), and poly(L-lactic acid).

41. The method of claim 39, wherein said poly(lactone) is selected from the group consisting of poly($\epsilon$-caprolactone), poly($\delta$-valerolactone), and poly($\gamma$-butyrolactone).

42. The method of claim 37, wherein said degradable region comprises poly(caprolactone).

43. The method of claim 37, wherein said polymerizable end groups contain a carbon—carbon double bond capable of polymerizing said macromer.

44. The method of claim 37, wherein said macromer comprises:

(a) a water soluble region comprising three-armed poly(ethylene glycol) with a molecular weight of 3,000 to 6,000 daltons;

(b) lactate groups on either side of region in (a); and (c) acrylate groups capping the region in (b).

45. The method of claim 37, wherein said macromer comprises:

(a) a water soluble region comprising poly(ethylene glycol) with a molecular weight of either 2,000 or 3,400 daltons;

(b) lactate groups on either side of region in (a); and (c) acrylate groups capping either side of the region in (b).

46. The method of claim 37, wherein said macromer comprises:

(a) a water soluble region comprising poly(ethylene glycol) with a molecular weight of 3,400 daltons;

(b) caprolactone groups on either side of region in (a); and (c) acrylate groups capping either side of the region in (b).

47. The method of claim 34, wherein said therapeutic article is administered to the lung of said mammal.

48. The method of claim 34, wherein said therapeutic article is administered by a route selected from the group consisting of intravenously, subcutaneously, intramuscularly, orally, and nasally.

49. The biocompatible therapeutic article of claim 1, wherein said biologically active substance is a protein.

50. The biocompatible therapeutic article of claim 49, wherein said protein is chosen from a group consisting of hormones, antibodies, differentiation factors, angiogenic factors, enzymes, cytokines, chemokines, interferons, colony-stimulating factors, and growth factors.

51. The biocompatible therapeutic article of claim 50, wherein said protein is human growth hormone.

52. The method of claim 22 or 34, wherein said biologically active substance is a protein.

53. The method of claim 52, wherein said protein is chosen from a group consisting of hormones, antibodies, differentiation factors, angiogenic factors, enzymes, cytokines, chemokines, interferons, colony-stimulating factors, and growth factors.

54. The method of claim 53, wherein said protein is human growth hormone.

55. The method of claim 22 or 34, wherein said therapeutic article releases at least 80% of said biologically active substance at a time 1¼ times greater than $t_{50}$.

56. The method of claim 22 or 34, wherein at least 80% of said particles have a particle size of less than about 80 microns.

57. The method claim 22 or 34, wherein said water soluble region consists essentially of poly(ethylene glycol) having a molecular weight of about 1,000 to 10,000 daltons.

58. The method of claim 22 or 34, wherein said degradable region comprises a blend of at least two different polymers.

59. The method of claim 22 or 34, wherein said macromer is degradable.

60. The method of claim 22 or 34, wherein said therapeutic article is capable of releasing said biologically active substance for a period of time at least 2 times greater than $t_{50}$.

61. The method of claim 22 or 34, wherein said therapeutic article delivers a therapeutic dose of said biologically active substance for a period of time at least 1¼ times greater than $t_{50}$.

62. The method of claim 22, wherein said mixture of molecules comprises a positively charged ion-carrying reagent when the pH is such that the protein is negatively charged.

63. The method of claim 62, wherein said positively charged ion-carrying reagent is triethanolamine.

64. The method of claim 62, wherein said positively charged ion-carrying reagent is Tris.

65. The method of claim 22, wherein said mixture of molecules comprises a negatively charged ion-carrying reagent when the pH is such that the protein is positively charged.

66. The method of claim 65, wherein said positively charged ion-carrying reagent is sodium dodecyl sulfate.

67. The method of claim 22, wherein said mixture of molecules comprises a surfactant.

68. The method of claim 67, wherein said surfactant is selected from the group consisting of Tween 20, Tween 80, and poloxamer F68.

69. The biocompatible therapeutic article of claim 1, wherein said mixture of molecules comprises a positively charged ion-carrying reagent when the pH is such that the protein is negatively charged.

70. The biocompatible therapeutic article of claim 69, wherein said positively charged ion-carrying reagent is triethanolamine.

71. The biocompatible therapeutic article of claim 69, wherein said positively charged ion-carrying reagent is Tris.

72. The biocompatible therapeutic article of claim 1, wherein said mixture of molecules comprises a negatively charged ion-carrying reagent when the pH is such that the protein is positively charged.

73. The biocompatible therapeutic article of claim 72, wherein said negatively charged ion-carrying reagent is sodium dodecyl sulfate.

74. The biocompatible therapeutic article of claim 1, wherein said mixture of molecules comprises a surfactant.

75. The biocompatible therapeutic article of claim 74, wherein said surfactant is selected from the group consisting of Tween 20, Tween 80, and poloxamer F68.

76. The biocompatible therapeutic article of claim 1, wherein said molecule or mixture of molecules is present in amounts sufficient to reduce the solubility of said biologically active substance in said article to less than 1 mg/ml.

77. The method of claim 22, wherein said molecule or mixture of molecules is present in amounts sufficient to reduce the solubility of said biologically active substance in the mixture of step (b) to less than 1 mg/ml.

* * * * *